US009044596B2

(12) United States Patent
Mahadevan-Jansen et al.

(10) Patent No.: US 9,044,596 B2
(45) Date of Patent: Jun. 2, 2015

(54) METHOD AND APPARATUS OF PULSED INFRARED LIGHT FOR CENTRAL NERVOUS SYSTEM NEURONS

(75) Inventors: Anita Mahadevan-Jansen, Nashville, TN (US); Jonathan Cayce, Nashville, TN (US); Robert Friedman, Nashville, TN (US); Anna Roe, Nashville, TN (US); E. Duco Jansen, Nashville, TN (US); Mykyta Chernov, Nashville, TN (US); Peter E. Konrad, Old Hickory, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 28 days.

(21) Appl. No.: 13/480,012

(22) Filed: May 24, 2012

(65) Prior Publication Data
US 2013/0013030 A1    Jan. 10, 2013

Related U.S. Application Data

(60) Provisional application No. 61/489,522, filed on May 24, 2011.

(51) Int. Cl.
*A61N 5/067* (2006.01)
*A61N 5/06* (2006.01)

(52) U.S. Cl.
CPC .......... *A61N 5/0622* (2013.01); *A61N 2005/063* (2013.01); *A61N 2005/0659* (2013.01); *A61N 2005/067* (2013.01)

(58) Field of Classification Search
CPC ........... A61N 5/0622; A61N 2005/063; A61N 2005/067; A61N 2005/0659
USPC ...................................... 607/88–89
See application file for complete search history.

(56) References Cited

U.S. PATENT DOCUMENTS

| 2005/0216072 A1* | 9/2005 | Mahadevan-Jansen et al. ............................... 607/89 |
| 2006/0161227 A1* | 7/2006 | Walsh et al. .................... 607/88 |

(Continued)

FOREIGN PATENT DOCUMENTS

WO    WO 2011120540 A1 * 10/2011

OTHER PUBLICATIONS

Mahadevan-Jansen et al., "Imaging optically induced neural activity in the brain", Aug. 31-Sep. 4, 2010, 32nd Annual International Conference of the IEEE EMBS, pp. 3379-3381.*

(Continued)

*Primary Examiner* — Gary Jackson
*Assistant Examiner* — Boniface N Nganga
(74) *Attorney, Agent, or Firm* — Morris Manning & Martin LLP; Tim Tingkang Xia, Esq.

(57) ABSTRACT

Certain aspects of the present disclosure are directed to a method of applying infrared neural stimulation (INS) to the central nervous system (CNS) of a target. The methods includes applying a pulsed infrared laser at a stimulation site in the CNS; and evoking responses from a region of interest of the CNS that is at or adjacent to the stimulation site by the pulsed infrared laser. In the method, the pulsed infrared laser penetrates a predetermined penetration depth of the stimulation site. Certain aspects of the present disclosure are directed to an apparatus for applying INS to the CNS of a target. The apparatus includes a generator generating a pulsed infrared laser, which penetrates a predetermined penetration depth of a stimulation site to evoke a response from the CNS, and an optical medium adapted for delivering the pulsed infrared laser at the stimulation site of the CNS.

30 Claims, 12 Drawing Sheets

(56) References Cited

U.S. PATENT DOCUMENTS

| | | | |
|---|---|---|---|
| 2008/0077198 A1* | 3/2008 | Webb et al. | 607/88 |
| 2008/0269847 A1* | 10/2008 | Nemenov | 607/89 |
| 2009/0069871 A1* | 3/2009 | Mahadevan-Jansen et al. | 607/89 |
| 2010/0324631 A1* | 12/2010 | Tass et al. | 607/88 |
| 2011/0295331 A1* | 12/2011 | Wells et al. | 607/3 |
| 2011/0295347 A1* | 12/2011 | Wells et al. | 607/89 |

OTHER PUBLICATIONS

Agmon, A., Connors, B.W., 1991. Thalamocortical responses of mouse somatosensory (barrel) cortex in vitro. Neuroscience 41, 365-379.

Blanton, M.G., Lo Turco, J.J., Kriegstein, A.R., 1989. Whole cell recording from neurons in slices of reptilian and mammalian cerebral cortex. J. Neurosci. Methods 30, 203-210.

Bouchard, M.B., Chen, B.R., Burgess, S.A., Hillman, E.M.C., 2009. Ultra-fast multispectral optical imaging of cortical oxygenation, blood flow, and intracellular calcium dynamics. Opt. Express 17, 15670-15678.

Bowser, D.N., Khakh, B.S., 2004. ATP excites interneurons and astrocytes to increase synaptic inhibition in neuronal networks. J. Neurosci. 24, 8606-8620.

Cayce, J.M., Kao, C.C., Malphrus, J.D., Konrad, P.E., Mahadevan-Jansen, A., Jansen, E.D., 2010. Infrared neural stimulation of thalamocortical brain slices. STQE. IEEE J. 16, 565-572.

Chapin, J.K., Lin, C.S., 1984. Mapping the body representation in the SI cortex of anesthetized and awake rats. J. Comp. Neurol. 229, 199-213.

Chen, L.M., Turner, G.H., Friedman, R.M., Zhang, N., Gore, J.C., Roe, A.W., Avison, M.J., 2007. High-resolution maps of real and illusory tactile activation in primary somatosensory cortex in individual monkeys with functional magnetic resonance imaging and optical imaging. J. Neurosci. 27, 9181-9191.

Cunha, R.A., 2008. Different cellular sources and different roles of adenosine: A1 receptor-mediated inhibition through astrocytic-driven volume transmission and synapse-restricted A2A receptor-mediated facilitation of plasticity. Neurochem. Int. 52, 65-72.

Das, A., Gilbert, C.D., 1995. Long-range horizontal connections and their role in cortical reorganization revealed by optical recording of cat primary visual cortex. Nature 375, 780-784.

Derdikman, D., Hildesheim, R., Ahissar, E., Arieli, A., Grinvald, A., 2003. Imaging spatiotemporal dynamics of surround inhibition in the barrels somatosensory cortex. J. Neurosci. 23, 3100-3105.

Duke, A.R., Cayce, J.M., Malphrus, J.D., Konrad, P., Mahadevan-Jansen, A., Jansen, E.D., 2009. Combined optical and electrical stimulation of neural tissue in vivo. J. Biomed. Opt. 14, 060501-060503.

Dunn, A.K., Devor, A., Dale, A.M., Boas, D.A., 2005. Spatial extent of oxygen metabolism and hemodynamic changes during functional activation of the rat somatosensory cortex. Neuroimage 27, 279-290.

Feng, H.-J., Kao, C., Gallagher, M.J., Jansen, E.D., Mahadevan-Jansen, A., Konrad, P.E., Macdonald, R.L., 2010. Alteration of GABAergic neurotransmission by pulsed infrared laser stimulation. J. Neurosci. Methods 192, 110-114.

Fried, N.M., Lagoda, G.A., Scott, N.J., Su, L.-M., Burnett, A.L., 2008. Noncontact stimulation of the cavernous nerves in the rat prostate using a tunable-wavelength thulium fiber laser. J. Endourol. 22, 409-414.

Fritsch, G., Hitzig, E., 1870. Ueber die elektrische Erregbarkeit der Grosshirns. Arch. Anat. Physiol. Wiss. Med. 37, 300-332.

Ghose, G.M., 2009. Attentional modulation of visual responses by flexible input gain. J. Neurophysiol. 101, 2089-2106.

[A18] Grinvald, A., 1985. Real-time optical mapping of neuronal activity: from single growth cones to the intact mammalian brain. Annu. Rev. Neurosci. 8, 263-305.

Grinvald, A., Lieke, E.E., Frostig, R.D., Hildesheim, R., 1994. Cortical point-spread function and long-range lateral interactions revealed by real-time optical imaging of macaque monkey primary visual cortex. J. Neurosci. 14, 2545-2568.

Hale, G.M., Querry, M.R., 1973. Optical constants of water in the 200-nm to 200-μm wavelength region. Appl. Opt. 12, 555-563.

Helmstaedter, M., Staiger, J.F., Sakmann, B., Feldmeyer, D., 2008. Efficient recruitment of layer 2/3 interneurons by layer 4 input in single columns of rat somatosensory cortex. J. Neurosci. 28, 8273-8284.

Hillman, E.M.C., 2007. Optical brain imaging in vivo: techniques and applications from animal to man. J. Biomed. Opt. 12, 051402-051428.

Izzo, A.D., Richter, C.-P., Jansen, E.D., Joseph, T., Walsh, J., 2006. Laser stimulation of the auditory nerve. Lasers Surg. Med. 38, 745-753.

Izzo, A.D., Walsh, J.T., Ralph, H., Webb, J., Bendett, M., Wells, J., Richter, C.-P., 2008. Laser stimulation of auditory neurons: effect of shorter pulse duration and penetration depth. Biophys. J. Biophys. 107, 117150.

Jenkins, M.W., Duke, A.R., GuS, DoughmanY, Chiel, H.J., FujiokaH, WatanabeM, Jansen, E.D., Rollins, A.M., 2010. Optical pacing of the embryonic heart. Nat. Photon. 4, 623-626.

Jones, M., Berwick, J., Johnston, D., Mayhew, J., 2001. Concurrent optical imaging spectroscopy and laser-Doppler flowmetry: the relationship between blood flow, oxygenation, and volume in rodent barrel cortex. Neuroimage 13, 1002-1015.

Kao, C.Q., Coulter, D.A., 1997. Physiology and pharmacology of corticothalamic stimulation-evoked responses in rat somatosensory thalamic neurons in vitro. J. Neurophysiol. 77, 2661-2676.

Koizumi, S., Fujishita, K., Tsuda, M., Shigemoto-Mogami, Y., Inoue, K., 2003. Dynamic inhibition of excitatory synaptic transmission by astrocyte-derived ATP in hippocampal cultures. Proc. Natl. Acad. Sci. USA 100, 11023-11028.

Kozlov, A.S., Angulo, M.C., Audinat, E., Charpak, S., 2006. Target cell-specific modulation of neuronal activity by astrocytes. Proc. Natl. Acad. Sci. 103, 10058-10063.

Levitt, J.B., Lund, J.S., 1997. Contrast dependence of contextual effects in primate visual cortex. Nature 387, 73-76.

Paxinos, G., Watson, C., 2007. The Rat Brain in Stereotaxic Coordinates/George Paxinos, Charles Watson. Elsevier, Amsterdam.

Perea, G., Navarrete, M., Araque, A., 2009. Tripartite synapses: astrocytes process and control synaptic information. Trends Neurosci. 32, 421-431.

Petersen, C.C.H., 2007. The functional organization of the barrel cortex. Neuron 56, 339-355.

Rajguru, S.M., Matic, A.I., Robinson, A.M., Fishman, A.J., Moreno, L.E., Bradley, A., Vujanovic, I., Breen, J., Wells, J. D., Bendett, M., Richter, C.-P., 2010. Optical cochlear implants: Evaluation of surgical approach and laser parameters in cats. Hear. Res. 269, 102-111.

Richter, C.P., Matic, A.l., .Wells, J.D., Jansen, E.D., Walsh, J.T., 2010. Neural stimulation with optical radiation. Laser Photon. Rev. 5, 68-80.

Roe, A.W., 2007. Long-term optical imaging of intrinsic signals in anesthetized and awake monkeys. Appl. Opt. 46, 1872-1880.

Roux, F.E., Tremoulet, M., 2002. Organization of language areas in bilingual patients: a cortical stimulation study. J. Neurosurg. 97, 857-864.

Schummers, J., Yu, H., Sur, M., 2008. Tuned responses of astrocytes and their influence on hemodynamic signals in the visual cortex. Science 320, 1638-1643.

Simons, D.J., Carvell, G.E., 1989. Thalamocortical response transformation in the rat vibrissa/barrel system. J. Neurophysiol. 61, 311-330.

Starr, P.A., Christine, C.W., Theodosopoulos, P.V., Lindsey, N., Byrd, D., Mosley, A., Marks Jr., W.J., 2002. Implantation of deep brain stimulators into the subthalamic nucleus: technical approach and magnetic resonance imaging-verified lead locations. J. Neurosurg. 97, 370-387.

Takano, T., Tian, G.-F., Peng, W., Lou, N., Libionka, W., Han, X., Nedergaard, M., 2006. Astrocyte-mediated control of cerebral blood flow. Nat. Neurosci. 9, 260-267. Takata, N., Hirase, H., 2008. Cortical layer 1 and layer 2/3 astrocytes exhibit distinct calcium dynamics in vivo. PLoS One 3, e2525.

(56) References Cited

OTHER PUBLICATIONS

Teudt, I.U., Nevel, A.E., Izzo, A.D., Walsh Jr., J.T., Richter, C.P., 2007. Optical stimulation of the facial nerve: a new monitoring technique? Laryngoscope 117, 1641-1647.
Toth, L.J., Rao, S.C., Kim, D.S., Somers, D., Sur, M., 1996. Sub-threshold facilitation and suppression in primary visual cortex revealed by intrinsic signal imaging. Proc. Natl. Acad. Sci. USA 93, 9869-9874.
Ts'o, D.Y., Frostig, R.D., Lieke, E.E., Grinvald, A., 1990. Functional organization of primate visual cortex revealed by high resolution optical imaging. Science 249, 417-420.
Tsytsarev, V., Pope, D., Pumbo, E., Garver, W., 2010. Intrinsic optical imaging of directional selectivity in rat barrel cortex: application of a multidirectional magnetic whisker stimulator. J. Neurosci. Methods 189, 80-83.
van Gemert, M.J.C., Welch, A.J., 1995. Approximate solutions for heat conduction: time constants. In: Welch, A.J., van Gemert, M.J.C. (Eds.), Optical-Thermal Response of Laser-Irradiated Tissue. Plenum Press, New York.
Vanzetta, I., Hildesheim, R., Grinvald, A., 2005. Compartment-resolved imaging of activity-dependent dynamics of cortical blood volume and oximetry. J. Neurosci. 25, 2233-2244.
Wang, X., Lou, N., Xu, Q., Tian, G.-F., Peng, W.G., Han, X., Kang, J., Takano, T., Nedergaard, M., 2006. Astrocytic Ca2+ signaling evoked by sensory stimulation in vivo. Nat. Neurosci. 9, 816-823.
Wells, J., Kao, C., Jansen, E.D., Konrad, P., Mahadevan-Jansen, A., 2005a. Application of infrared light for in vivo neural stimulation. J. Biomed. Opt. 10, 064003.
Wells, J., Kao, C., Mariappan, K., Albea, J., Jansen, E.D., Konrad, P., Mahadevan-Jansen, A. 2005b. Optical stimulation of neural tissue in vivo. Opt. Lett. 30, 504-506.
Wells, J., Kao, C., Konrad, P., Milner, T., Kim, J., Mahadevan-Jansen, A., Jansen, E.D., 2007a. . . Biophysical mechanisms of transient optical stimulation of peripheral nerve. Biophys. J. 93, 2567-2580.
Wells, J., Konrad, P., Kao, C., Jansen, E.D., Mahadevan-Jansen, A., 2007b. Pulsed laser versus electrical energy for peripheral nerve stimulation. J. Neurosci. Methods 163, 326-337.
Wininger, F.A., Schei, J.L., Rector, D.M., 2009. Complete optical neurophysiology: toward optical stimulation and recording of neural tissue. Appl. Opt. 48, D218-D224.
S. D. Schoonhoven, "Models and analysis of compound nerve action potentials. ," Crit. Rev. Biomed. Eng., v.19, 47-111, 1991.
B. Hille, Ion Channels of Excitable Membranes, 3 ed. Sunderland, MA: Sinaure Associates, 2001.
C. Huang "Characterization of voltage-gated sodium channel blockers by electrical stimulation and fluorescence detection of membrane potential," Nat. Biotechnology, vol. 24,. 439-446, 2006.
R. Plonsey and R. Barr, Bioelectricity: A Quantitative Approach, 2 ed.: Kluwer Academic, 2000.
E. Civillico and D. Contreras, "Comparison of Responses to Electrical Stimulation and Whisker Deflection Using Two Different Voltage-Sensitive Dyes in Mouse Barrel Cortex in Vivo," Journal of Membrane Biology, vol. 208, pp. 171-182, 2005.
K. McGill, et. al, "On the nature and elimination of stimulus artifact in nerve signals evoked and recorded using surface electrodes," IEEE Trans Biomed Eng, vol. 29, pp. 129-37, 1982.
J. Wells, S. Thomsen, P. Whitaker, E. D. Jansen, C. C. Kao, P. E. Konrad, and A. Mahadevan-Jansen, "Optically mediated nerve stimulation: Identification of injury thresholds," Lasers Surg Med, vol. 39, pp. 513-526, Jul. 2007.
W. H. Wu, R. Ponnudurai, J. Katz, C. B. Pott, R. Chilcoat, A. Uncini, S. Rapoport, P. Wade, and A. Mauro, "Failure to confirm report of light-evoked response of peripheral nerve to low power helium-neon laser light stimulus," Brain Res, vol. 401, pp. 407-408, Jan. 20, 1987.
P. Balaban, R. Esenaliev, T. Karu, E. Kutomkina, V. Letokhov, A. Oraevsky, and N. Ovcharenko, "He-Ne laser irradiation of single identified neurons," Lasers Surg Med, vol. 12, pp. 329-337, 1992.
D. Bragard, A. C. Chen, and L. Plaghki, "Direct isolation of ultra-late (C-fibre) evoked brain potentials by CO2 laser stimulation of tiny cutaneous surface areas in man," Neurosci Lett, vol. 209, pp. 81-84, May 10, 1996.
D. Gigo-Benato, et al., "Low-power laser biostimulation enhances nerve repair after end-to-side neurorrhaphy: a double-blind randomized study in the rat median nerve model," Lasers in Medical Science, vol. 19, pp. 57-65, 2004.
S. Ilic, S. Leichliter, J. Streeter, A. Oron, L. DeTaboada, and U. Oron, "Effects of Power Densities, Continuous and Pulse Frequencies, and Number of Sessions of Low-Level Laser Therapy on Intact Rat Brain," Photomedicine and Laser Surgery, vol. 24, pp. 458-466, 2006.
E. S. Boyden, F. Zhang, E. Bamberg, G. Nagel, and K. Deisseroth, "Millisecond-timescale, genetically targeted optical control of neural activity," Nat Neurosci, vol. 8, pp. 1263-1268, Sep. 2005.
A. D. Izzo, J. T. Walsh, Jr., E. D. Jansen, M. Bendett, and C. P. Richter, "Optical parameter variability in laser nerve stimulation: a study of pulse duration, repetition rate, and wavelength," IEEE Trans Biomed Eng, vol. 54, pp. 1108-1114, Jun 2007.
N. Takata and H. Hirase, "Cortical layer 1 and layer 2/3 astrocytes exhibit distinct calcium dynamics in vivo," PLoS One, vol. 3, p. e2525, 2008.
Cayce, JM, et el. Pulsed Infrared Light Alters Neural Activity in Rat Somatasensory Cortex in Vivo. NeuroImage. Apr. 12, 2011, vol. 57.

\* cited by examiner

METHOD AND APPARATUS OF PULSED INFRARED LIGHT FOR CENTRAL NERVOUS SYSTEM NEURONS

CROSS-REFERENCE TO RELATED APPLICATIONS

This application claims priority to and the benefit of, pursuant to 35 U.S.C. §119(e), U.S. provisional patent application Ser. No. 61/489,522, filed on May 24, 2011, entitled "METHOD AND APPARATUS OF PULSED INFRARED LIGHT FOR THE INHIBITION OF CENTRAL NERVOUS SYSTEM NEURONS," by Anita Mahadevan-Jansen et al., the disclosure of which is incorporated herein in its entirety by reference.

Some references, which may include patents, patent applications and various publications, are cited and discussed in the description of this disclosure. The citation and/or discussion of such references is provided merely to clarify the description of the present disclosure and is not an admission that any such reference is prior art to the disclosure described herein. All references cited and discussed in this specification are incorporated herein by reference in their entireties and to the same extent as if each reference was individually incorporated by reference. In terms of notation, hereinafter, "[first author name, publish year]" or "[identifier]" represent the corresponding reference cited in the reference lists. For example, "[Izzo et al., 2008]" represents the reference listed in the Reference List A of which the first author is Izzo and which was published in 2008, namely, "[A24] Izzo, A. D., Walsh, J. T., Ralph, H., Webb, J., Bendett, M., Wells, J., Richter, C.-P., 2008. Laser stimulation of auditory neurons: effect of shorter pulse duration and penetration depth. Biophys. J. Biophys. 107, 117150." "[B10]" represents the reference identified as B10 in the Reference List B, namely, "[B10] J. Wells, C. Kao, P. Konrad, T. Milner, J. Kim, A. Mahadevan-Jansen, and E. D. Jansen, "Biophysical mechanisms of transient optical stimulation of peripheral nerve," Biophys J, vol. 93, pp. 2567-80, Oct. 1, 2007."

STATEMENT OF FEDERALLY-SPONSORED RESEARCH

This invention was made with Government support under contract nos. RO1 NS052407-01 and RO1 NS 44375, awarded by the National Institute of Health. The Government has certain rights in the invention.

FIELD

The present disclosure is in the field of neural stimulation and, in particular, infrared neural stimulation (INS) of the central nervous system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Neural stimulation is typically the process of using an external source to activate ion channels causing depolarization of the neural membrane and evoking an action potential to propagate down the axon of a stimulated neuron. Electrical, thermal, chemical, optical and mechanical methods have been reported to generate action potentials in both the central nervous system (CNS) and peripheral nervous system (PNS) [B1]. Electrical stimulation has been the gold standard for the stimulation of neurons for both clinical and basic research applications. For nearly two centuries, neurons have been activated by electrical stimulation through the injection of a current or change in voltage delivered via an electrode placed on or near the neural tissue. The injected current or change in voltage causes an increase in the transmembrane potential to activate voltage-gated ion channels which generates action potential propagation down the neuron's axon [B2-5]. However, electrical stimulation can have limited spatial precision due to inherent electrical field spread which can recruit unwanted neural tissue, and electrical stimulation results in a stimulation artifact which can mask relevant neuronal signals resulting from the stimulation event [B6, 7].

SUMMARY

Certain aspects of the present disclosure are directed to a method of applying infrared neural stimulation (INS) to the central nervous system (CNS) of a target. The methods includes: applying a pulsed infrared laser at a stimulation site in the CNS; and evoking responses from a region of interest of the CNS that is at or adjacent to the stimulation site by the pulsed infrared laser. In the method, the pulsed infrared laser penetrates a predetermined penetration depth of the stimulation site.

In certain embodiments, the pulsed infrared laser is applied to the stimulation site in vivo. In certain embodiments, the penetration depth is in a range of about 10 µm to about 400 µm. In certain embodiments, the penetration depth is in a range of about 300 µm to about 600 µm. In certain embodiments, the penetration depth is in a range of about 500 µm to about 2,000 µm.

In certain embodiments, the pulsed infrared laser has a wavelength in a range of about 1.4 µm to about 1.6 µm. In certain embodiments, the pulsed infrared laser has a wavelength in a range of about 1.8 µm to about 2.2 µm. In certain embodiments, the pulsed infrared laser has a wavelength of about 1.875 µm. In certain embodiments, the pulsed infrared laser has a wavelength of about 1.45 µm. In certain embodiments, the pulsed infrared laser has a wavelength of about 1.94 µm.

In certain embodiments, the pulsed infrared laser reaches primarily layers I and II of neural tissues of the stimulation site where inhibitory neurons are a predominant cellular component. In certain embodiments, the pulsed infrared laser reaches primarily layers III, IV, V, and VI of neural tissues of the stimulation site where excitatory neurons are a predominant cellular component. In certain embodiments, the stimulation site has primarily inhibitory circuits and the evoked responses are primarily inhibitory neural responses. In certain embodiments, the stimulation site has primarily excitatory circuits and the evoked responses are primarily excitatory neural responses.

In certain embodiments, the pulsed infrared laser is delivered through one or more free optics to the stimulation site. In certain embodiments, the pulsed infrared laser is delivered through an optical fiber to the stimulation site. In certain embodiments, the optical fiber is positioned at a distance from a surface of the stimulation site in a range of about 0 to about 1,000 µm. In certain embodiments, the optical fiber has a predetermined diameter and is positioned at a predetermined distance from the stimulation site such that the pulsed infrared laser delivered through the optical fiber covers a surface of the stimulation site entirely. In certain embodiments, the optical fiber has a diameter in a range of about 5 μm to about 1,000 μm. In certain embodiments, the optical fiber has a numerical aperture in a range of about 0.1 to about 0.4. In certain embodiments, the optical fiber has a diameter of about 400 μm and a numerical aperture of about 0.22.

In certain embodiments, the covered surface of the stimulation site has a spot size in a range of about 5 μm to about 2,000 μm. In certain embodiments, the pulsed infrared laser is applied with a repetition rate in a range of about 1 Hz to about 500 Hz. In certain embodiments, the pulsed infrared laser is applied with a repetition rate in a range of about 50 Hz to about 200 Hz. In certain embodiments, the pulsed infrared laser is applied through a pulse train having a duration in a range of about a single pulse to about 3 seconds. In certain embodiments, the pulsed infrared laser is applied with a predetermined pulse width in a range of about 5 ps to about 5 ms. In certain embodiments, the pulsed infrared laser is applied with a constant pulse width of 250 μs.

In certain embodiments, the pulsed infrared laser is applied with a radiant exposure in a range of about 0.01 J/cm$^2$ to about 1.00 J/cm$^2$. In certain embodiments, the stimulation site is positioned at a distance from the region of interest in a range of about 0 to about 2 mm. In certain embodiments, the stimulation site is positioned at a distance from the region of interest in a range of about 0 to about 1 mm.

Certain aspects of the present disclosure are directed to an apparatus for applying infrared neural stimulation (INS) to the central nervous system (CNS) of a target. The apparatus includes: a generator generating a pulsed infrared laser; and an optical medium adapted for delivering the pulsed infrared laser at a stimulation site of the CNS. The pulsed infrared laser of the apparatus is configured to penetrate a predetermined penetration depth of the stimulation site to evoke a response from the CNS.

In certain embodiments, the penetration depth is in a range of about 100 μm about 400 μm. In certain embodiments, the penetration depth is in a range of about 300 μm to about 600 μm. In certain embodiments, the penetration depth is in a range of about 500 μm to about 2,000 μm.

In certain embodiments, the pulsed infrared laser has a wavelength in a range of about 1.4 μm to 1.6 μm. In certain embodiments, the pulsed infrared laser has a wavelength in a range of about 1.8 μm to about 2.2 μm. In certain embodiments, the pulsed infrared laser has a wavelength of about 1.875 μm. In certain embodiments, the pulsed infrared laser has a wavelength of about 1.45 μm. In certain embodiments, the pulsed infrared laser has a wavelength of about 1.94 μm.

In certain embodiments, the optical medium is adapted to deliver the pulsed infrared laser to reach primarily layers I and II of the neural tissues of the stimulation site where inhibitory neurons are a predominant cellular component. In certain embodiments, the optical medium is adapted to deliver the pulsed infrared laser to reach primarily layers III, IV, V, and VI of the neural tissues of the stimulation site where excitatory neurons are a predominant cellular component. In certain embodiments, the optical medium is adapted to deliver the pulsed infrared laser to the stimulation site that has primarily inhibitory circuits and the evoked responses are primarily inhibitory neural responses. In certain embodiments, the optical medium is adapted to deliver the pulsed infrared laser to the stimulation site that has primarily excitatory circuits and the evoked responses are primarily excitatory neural responses.

In certain embodiments, the optical medium includes one or more free optics. In certain embodiments, the optical medium is an optical fiber. In certain embodiments, the optical fiber is adapted to be positioned at a distance from a surface of the stimulation site in a range of about 0 to about 1,000 μm. In certain embodiments, the optical fiber has a predetermined diameter and is adapted to be positioned at a predetermined distance from the stimulation site such that the infrared laser delivered through the optical fiber covers a surface of the stimulation site entirely. In certain embodiments, the optical fiber has a diameter in a range of about 5 μm to about 1,000 μm. In certain embodiments, the optical fiber has a numerical aperture in a range of about 0.1 to about 0.4. In certain embodiments, the optical fiber has a diameter of about 400 μm and a numerical aperture of about 0.22.

In certain embodiments, the optical fiber is adapted to cover a surface of the stimulation site that has a spot size in a range of about 5 μm to about 2,000 μm. In certain embodiments, the generator is adapted to generate the pulsed infrared laser having a repetition rate in a range of about 1 Hz to about 500 Hz. In certain embodiments, the generator is adapted to generate the pulsed infrared laser having a repetition rate in a range of about 50 Hz to about 200 Hz. In certain embodiments, the generator is adapted to generate the pulsed infrared laser having a pulse train duration in a range of about a single pulse to about 3 seconds. In certain embodiments, the generator is adapted to generate the pulsed infrared laser having a predetermined pulse width in a range of about 5 ps to about 5 ms. In certain embodiments, the generator is adapted to generate the pulsed infrared laser radiation having a constant pulse width of 250 μs.

In certain embodiments, the generator is adapted to generate the pulsed infrared laser having a radiant exposure in a range of about 0.01 J/cm$^2$ to about 1.00 J/cm$^2$. In certain embodiments, the optical medium is adapted to deliver the pulsed infrared laser to the stimulation site that is positioned at a distance from the region of interest in a range of about 0 to about 2 mm. In certain embodiments, the optical medium is adapted to deliver the pulsed infrared laser to the stimulation site that is positioned at a distance from the region of interest in a range of about 0 to about 1 mm.

In yet another aspect, the present application relates to a process for evoking responses from a region of interest of the central nervous system (CNS) of a target. In one embodiment, the process includes the step of applying a pulsed infrared laser at a stimulation site in the CNS such that the pulsed infrared laser penetrates a predetermined penetration depth of the stimulation site.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1A:
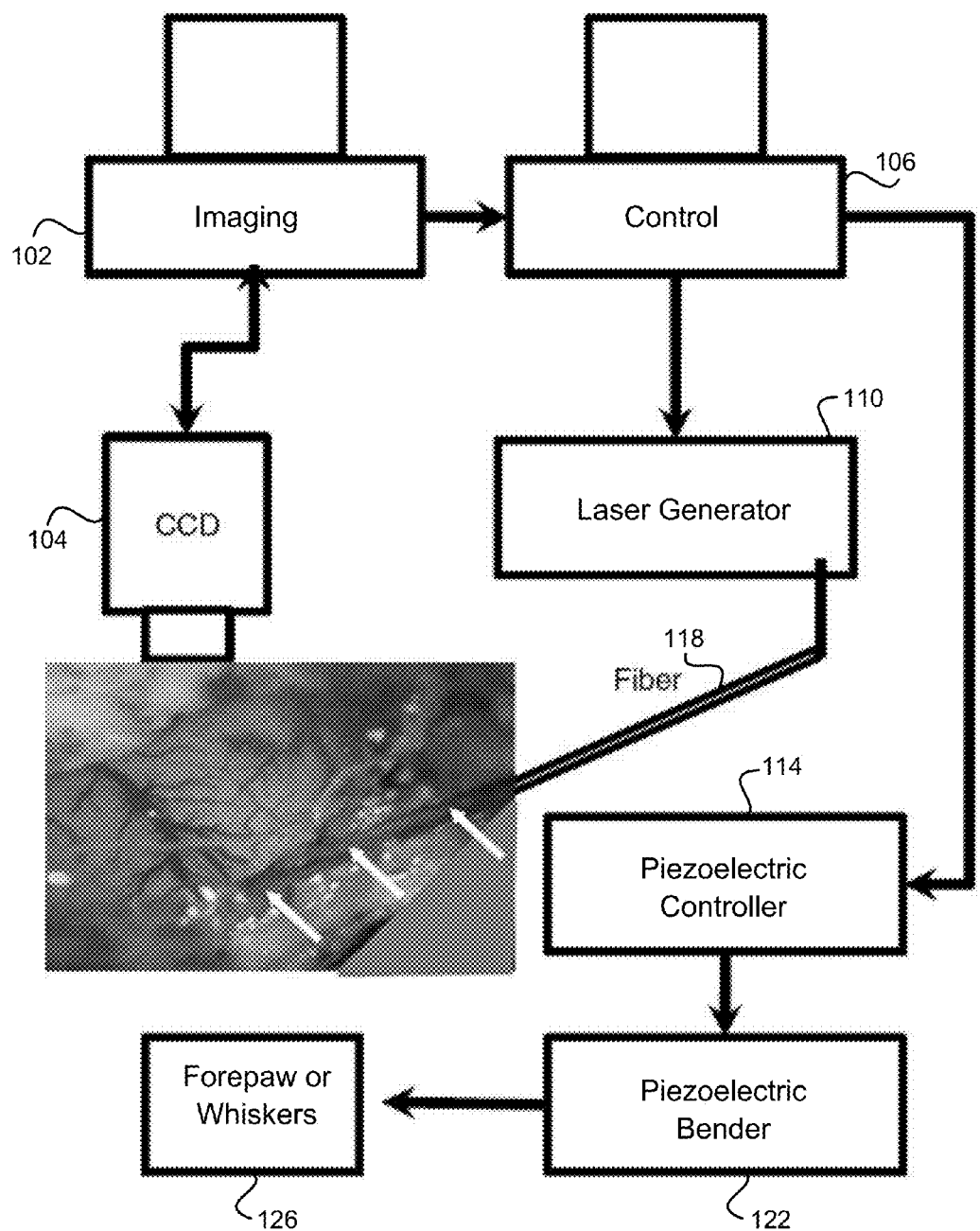
FIG. 1A is a schematic diagram of an experimental setup in accordance with certain embodiments of the present disclosure.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprising," "including," "carrying," "having," "containing," "involving," and the like are to be understood to be open-ended, i.e., to mean including but not limited to.

The description below is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

Overview

Infrared neural stimulation (INS) represents a relatively new stimulation modality that exhibits high spatial precision and can be delivered in a contact free method for the stimulation of neural tissue [Wells et al., 2005b]. Investigations into the use of pulsed infrared light to stimulate neural tissue began in the peripheral nervous system (PNS) where it is demonstrated the ability of INS to reliably evoke action potentials in peripheral nerves. Pulsed infrared light can also stimulate auditory ganglion cells in the cochlea with high spatial precision establishing INS as a possible alternative to electrical stimulation for cochlear implants [Izzo et al., 2008]; [Rajguru et al., 2010]; [Richter et al., 2010]. Most recently, embryonic quail hearts were paced by pulsed infrared light, suggesting the possibility of optically based pacemakers [Jenkins et al., 2010]. In the central nervous system (CNS) the first application of INS was demonstrated in thalamocortical brain slices [Cayce et al., 2010].

For each of these applications, the parameters set for INS had to be established. Stimulation of the sciatic and facial nerve required low frequency stimulation (maximum of 5 Hz) to evoke stimulus locked compound muscle action potentials; the threshold radiant exposures can be 0.4 $J/cm^2$ and 0.7 $J/cm^2$ for the sciatic and facial nerves, respectively [Teudt et al., 2007]; [Wells et al., 2007b]. Stimulation of rat cavernous nerves with infrared light at a radiant exposure of 1 $J/cm^2$ at 10 Hz for 60 s can produce a complex intracavernosal pressure response with no functional loss [Fried et al., 2008]. In cochlear studies, effective non-damaging stimulation parameters, consisting of high frequency (at least 200 Hz), short pulsewidth stimulation, evoked potentials in the inferior colliculus [Izzo et al., 2008]; [Rajguru et al., 2010]; [Richter et al., 2010]. The pacing of embryonic hearts required radiant exposures of 0.8 $J/cm^2$ at 2 Hz [Jenkins et al., 2010]. The different stimulation parameters across each of these studies illustrate that each new INS application requires the identification of unique laser parameters to best activate a new target tissue.

Certain aspects of the present disclosure are directed to stimulate neurons in the brain using INS technique. In certain embodiments, INS is a direct induction of an evoked potential or action potential in response to a transient targeted deposition of infrared energy into neural tissue [B8-10]. Typically, pulsed infrared energy can generate an action potential, whereas continuous wave irradiation may not lead to action potential propagation. Studies have shown that the induction of a temperature gradient (dT/dz or dT/dt) is required for pulsed infrared light to generate an action potential [B10]. In certain aspects, INS differs from other optical methods used to modulate the excitability of nerves [B11-13] or from the use of low-level light therapy where low irradiance levels of weakly absorbed light is continuously applied over several minutes to obtain a physiological response [B14, 15]. INS can activate neuronal mechanisms which are intrinsic to the excitable tissues of the organism. This differs from optical neural control using visible light to stimulate channel-rhodopsin channels which have been genetically engineered into cells and tissues that are normally not sensitive to light [B16].

In certain embodiments, possible applications of INS in the CNS include cortical mapping during awake craniotomies, tumor resection, and deep brain stimulation. All three potential applications stand to benefit from the lack of electrical field spread associated with INS and cortical mapping and tumor resection procedures could benefit from contact free delivery of infrared light reducing the possibility of mechanical damage to healthy tissue. The high spatial precision of INS can be another tool for understanding the function neural networks and possibly reveal neural signal which is masked by the stimulation artifact seen with electrical stimulation.

Unlike the PNS where axons of neurons are organized in parallel bundles in nerves, the brain is organized into a complex neuronal network. In other words, differences in geometry and physiology of the brain compared to the PNS exist. Certain aspects of the present disclosure are directed to pulsed infrared lasers having wavelengths specifically configured to achieve stimulation in the CNS. The wavelengths can be different from those of the INS applied to PNS. INS can activate neurons contained within a brain slice model. Certain aspects of the present disclosure are directed to repetition rates of the infrared light pulses, which are specifically configured for application to CNS. In certain embodiments, stimulation was best carried out using higher repetition rates than what was used for PNS stimulation.

Certain aspects of the present disclosure are directed to a novel technique that can manipulate cortex activities of a target in vivo. In certain embodiments, INS is used to evoke responses in the CNS of the target. In certain embodiments, INS can evoke responses in the sensory areas of the cerebral cortex, some of which can be similar to those evoked by natural sensory stimulation. The evoked responses can be similar to the responses in the visual cortex, auditory cortex, and somatosensory cortex evoked by the senses of vision, audition, and touch.

Infrared laser with predetermined parameters can be applied at or near a region of interest (ROI) of the cortex of a living target to evoke responses of that ROI. In certain embodiments, the laser is applied at a stimulation site that is at a distance within about 5 mm, preferably about 2 mm, and even more preferably about 1 mm, from a ROI. In certain embodiments, the spatial extent of the INS stimulus has a roughly 2 mm region of effect.

Wavelength of the laser that is applied to the CNS is determined based on certain criteria. In certain embodiments, wavelength selection for performing infrared neural stimulation was based on the optical penetration depth of light in tissue. In certain embodiments, the penetration depth is in a range of about 100 μm to about 400 μm. In certain embodiments, the penetration depth is in a range of about 300 μm to about 600 μm. In certain embodiments, the penetration depth is in a range of about 500 μm to about 2000 μm. For example, it can be estimated using absorption data for water since biological soft tissue is 70% water [Hale and Querry, 1973]. Certain studies using infrared light to stimulate tissue have indicated that an optical penetration depth of 300-600 μm is optimal for stimulating neural tissue [Cayce et al., 2010];

[Richter et al., 2010]; [Wells et al., 2005a]. This optical penetration depth range can correspond to a wavelength of 1.875 µm. It is determined that lasers having similar wavelengths can be applied to CNS to evoke responses in the cortex. In certain embodiments, infrared neural stimulation was performed using laser having a wavelength of about 1.875 µm. In certain embodiments, a laser having a wavelength of about 1.94 µm can be used. In certain embodiments, a laser having a wavelength in a range of about 1 µm to about 2.2 µm, preferably 1.4 µm to about 1.6 µm and about 1.8 µm to about 2.2 µm.

Pulsed infrared lasers can be delivered to the cortex through various optical mediums. In certain embodiments, an infrared laser is delivered through a optical fiber. For example, the optical fiber can have a diameter in a range of about 5 µm to about 1,000 µm. For example, the optical fiber can be 400 µm Ocean Optics fiber (St. Petersburg, Fla.) with a numerical aperture (NA) of 0.22. The fiber can be placed between about 0 and about 1000 µm from cortex. In certain embodiments, the pulsed infrared laser is delivered through one or more free optics to the stimulation site. Laser repetition rate is in a predetermined range and, in certain embodiments, ranges between about 10 and about 500 Hz, and preferably between about 50 and about 200 Hz. The pulse width can vary in a range of about 5 ps to about 5 ms according to needs and, in certain embodiments, can be held constant and for example at 250 µs. The average power from the laser can be configured in consideration of the characteristics of the CNS.

In certain embodiments, radiant exposure can be calculated based on the NA of the fiber and the distance of the fiber tip from cortex [Wells et al., 2005a]. The radiant exposure can be dependent on the stimulation parameters used for a given experiment. In certain embodiments, the radiant exposure can vary in a range of about 0.01 $J/cm^2$ to about 1.00 $J/cm^2$, and preferably about 0.01 $J/cm^2$ to 0.55 $J/cm^2$. The pulse train duration can be a predetermined value in a range of about single pulse to about 3 seconds and, for example, 500 ms.

Figure 4:
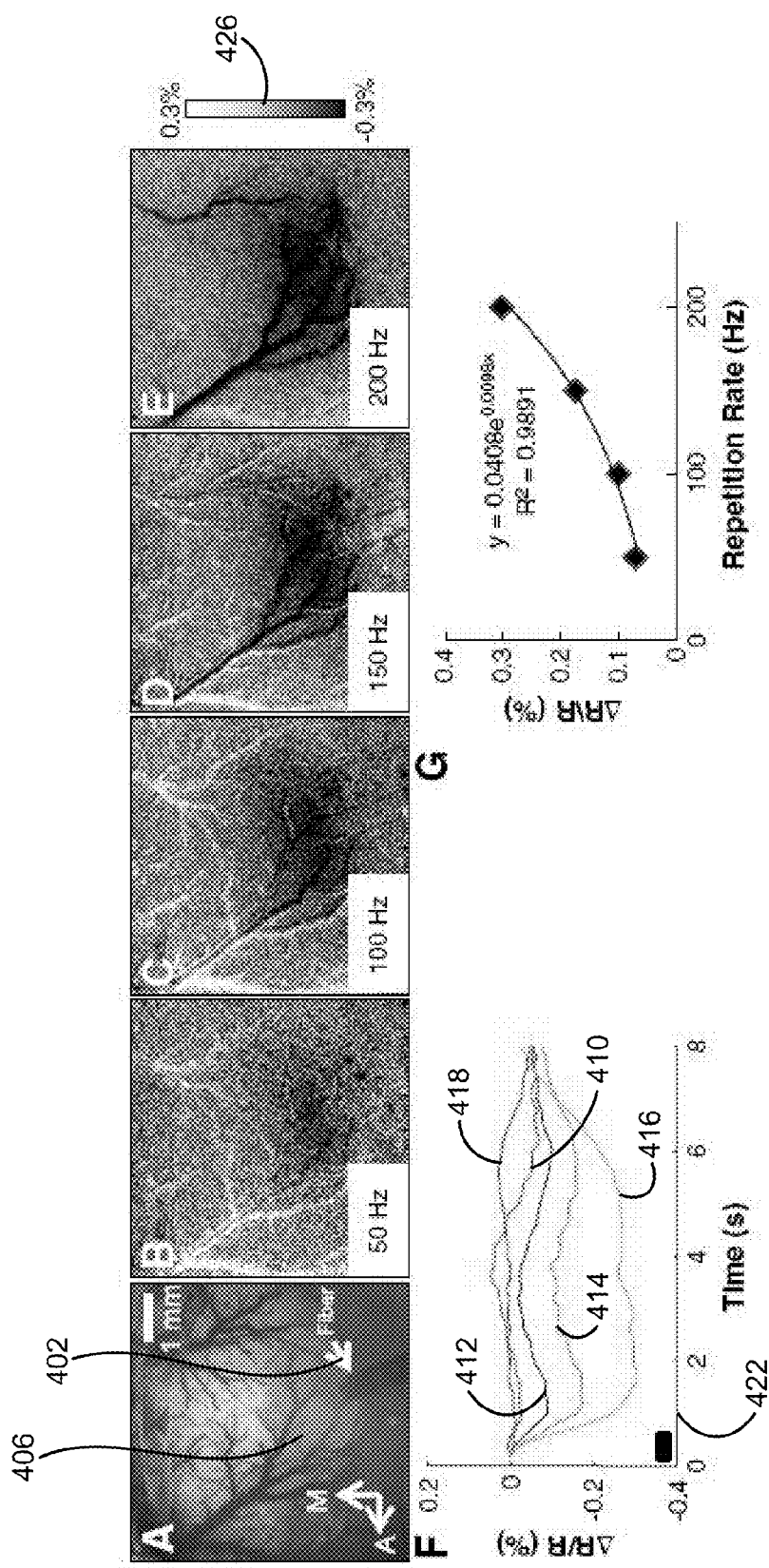
FIG. 4 illustrates intrinsic signals produced by different rates of INS in accordance with certain embodiments of the present disclosure.
Figure 5:
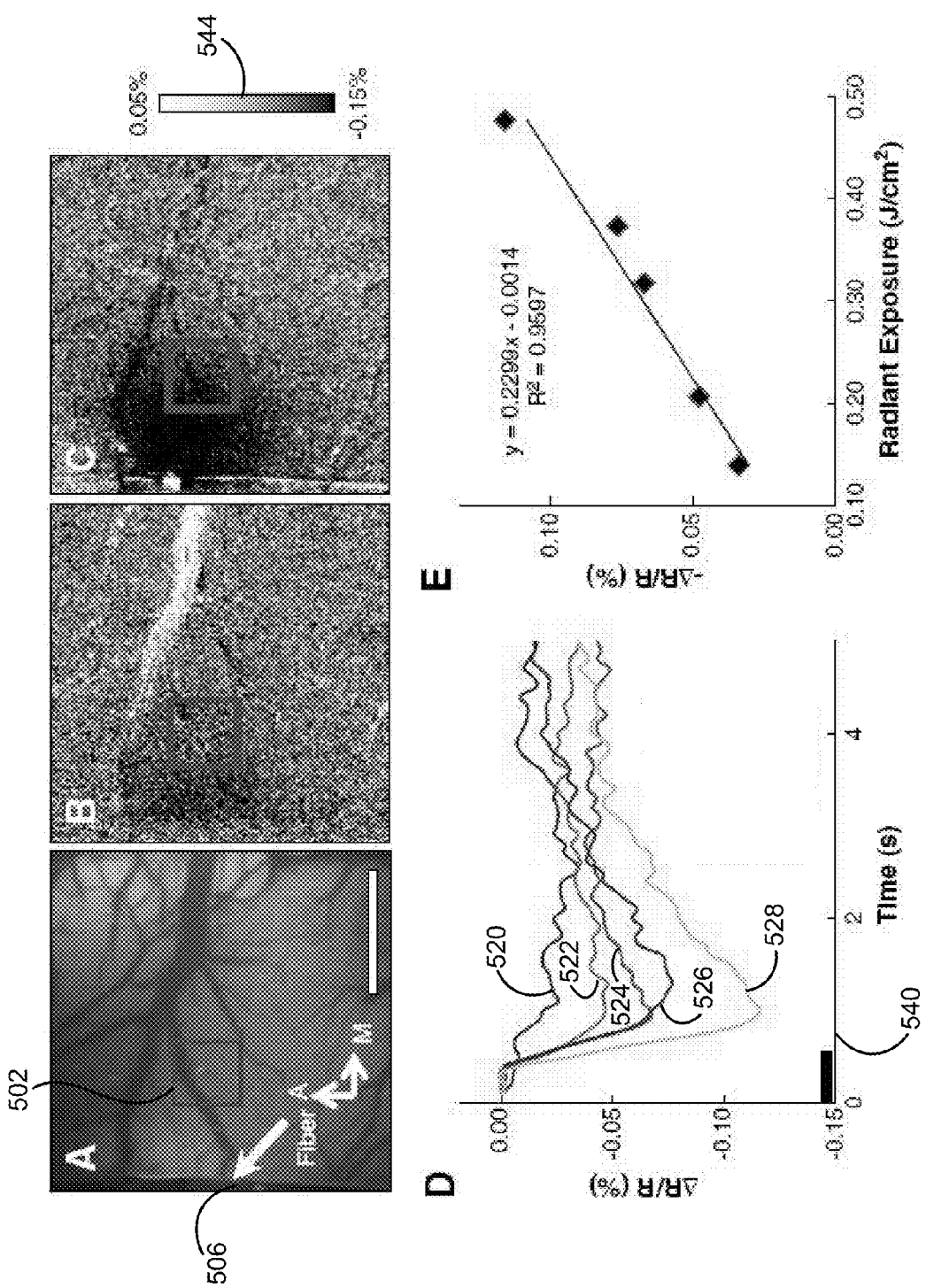
FIG. 5. shows that increased INS radiant exposure leads to an increase in intrinsic signal magnitude in accordance with certain embodiments of the present disclosure.

The magnitude of the response evoked by the INS increases with increasing infrared light energy, produced either by increasing the stimulation frequency or by increasing the radiant energy of the laser (FIGS. 4 and 5). In certain embodiments, changing the radiant exposure induces a linear response in peak magnitude of the evoked responses compared to an exponential response induced by changing the repetition rate.

In certain embodiments, the repetition rate and pulse width of the laser are adjusted or varied to affect the responses evoked in an ROI. In certain embodiments, the pulsed infrared laser is applied with a repetition rate in a range of about 10-500 Hz. In certain embodiments, the pulsed infrared laser is applied with a repetition rate in a range of about 50-200 Hz. In certain embodiments, the pulsed infrared laser radiation is applied with a predetermined constant or variable pulse width. The pulsed infrared laser radiation can be applied with a predetermined pulse width in a range of about 0.01 $J/cm^2$ to about 1.00 $J/cm^2$. The greater the total light energy applied to the cortex, the stronger the responses evoked in the cortex. For example, using a 500 ms duration pulse train and 250 µs pulse width, repetition rates of 50, 100, 150, and 200 Hz can be applied (FIGS. 4B-E). As can be seen qualitatively in FIG. 4B-E, an increase in laser repetition rate increased the size of the activation region. Quantitatively, in this example, the 200 Hz laser stimulus is used to produce the largest responses in the cortex, while a 50 Hz stimulus is used to produce the smallest response (FIG. 4F). As shown in FIG. 4G, the repetition rate of the laser is configured and varied to alter the magnitude of the responses of cortex. In certain embodiments, the magnitude of the evoked responses of cortex exhibits an exponential fit with the repetition rate of the laser.

Threshold is an important aspect of INS to consider when developing the modality as an alternative to electrical stimulation. In certain embodiments, the radiant exposure of the laser is configured and varied to evoked varied responses in the cortex. In certain embodiments, the pulsed infrared laser is applied with a radiant exposure in a range of about 0.01-0.55 $J/cm^2$. In certain embodiments, the magnitude of the evoked responses of the cortex exhibits a linear fit with radiant exposure (FIG. 5E).

For example, the laser parameters of stimulation can be 200 Hz, 500 ms duration pulse train of 250 µs pulses at the five different radiant exposures indicated in FIGS. 5B and C. The smaller radiant exposure (e.g. 0.14 $J/cm^2$) resulted in the smaller magnitude of the evoked responses of cortex. Intermediate radiant exposures (e.g. 0.21 and 0.32 and $J/cm^2$) produced intermediate magnitude of the evoked responses. The larger radiant exposures tested (0.37 and 0.48 $J/cm^2$) resulted the larger magnitude of the evoked responses. Further, the area of activation also increased with radiant exposure energy, as shown qualitatively (FIGS. 5B and C).

In certain embodiments, the laser stimulation site on the cortex is changed to evoke the varied responses at an ROI. The magnitude of the evoked responses is the largest when the stimulation site is closest to the ROI and decreases in accordance with distance between the ROI and the stimulation site.

The cerebral cortex of the brain consists of a neural network and contains inhibitory interneurons, and glial cells, astrocytes, ogliodendrocytes, and microglia, in a greater concentration than excitatory neurons. As understood by one skilled in the art, the neurons of the cerebral cortex can be typically grouped into six main layers, from outside (pial surface) to inside (white matter): Layer I, the Molecular layer, contains few scattered neurons and consists mainly of extensions of apical dendritic tufts of pyramidal neurons and horizontally-oriented axons, as well as glial cells. Some Cajal-Retzius and spiny stellate cells can be found here. Layer II, the External granular layer, contains small pyramidal neurons and numerous stellate neurons. Layer III, the External Pyramidal layer, contains predominantly small and medium-size pyramidal neurons, as well as non-pyramidal neurons with vertically-oriented intracortical axons. Layer IV, the Internal Granular layer, contains different types of stellate and pyramidal neurons, and is the main target of thalamocortical afferents from thalamus type C neurons as well as intra-hemispheric corticocortical afferents. Layer V, the Internal Pyramidal layer, contains large pyramidal neurons (such as the Betz cells in the primary motor cortex); there are large pyramidal cells which give rise to axons leaving the cortex and running down through the basal ganglia, the brain stem and the spinal cord. Layer VI, the Polymorphic or Multiform layer, contains few large pyramidal neurons and many small spindle-like pyramidal and multiform neurons; layer VI sends efferent fibers to the thalamus, establishing a very precise reciprocal interconnection between the cortex and the thalamus. These connections are both excitatory and inhibitory. Neurons send excitatory fibers to neurons in the thalamus and also from collateral to them ones via the thalamic reticular nucleus that inhibit these thalamus neurons or ones adjacent to them. The cortical layers are not simply stacked one over the other; there exist characteristic connections between different layers and neuronal types, which span all the thickness of the cortex. These cortical microcircuits are grouped into cortical columns and minicolumns.

In certain embodiments, the stimulation site has primarily inhibitory circuits and the evoked neural responses are primarily inhibitory responses. In certain embodiments, the stimulation site has primarily excitatory circuits and the evoked neural responses is primarily excitatory responses. Direct stimulation of cortex with laser can evoke responses in excitatory neurons that would then propagate in numerous directions making it difficult to detect evoked excitatory responses. INS can evoke direct responses in the smaller inhibitory neurons or glial cells. A confounding issue is the depth at which the infrared light penetrates into the tissue. For example, the wavelength of light (1.875 µm) penetrates approximately 300-600 µm into tissue, where intensity decays exponentially following Beer's law. This indicates that mainly layers I and II of cortex are stimulated; only a small percentage of photons reach layer III. A higher number of inhibitory neurons and astrocytes are present in layers I and II than excitatory neurons, which are mainly located in layers III/IV. However, the dendritic tree of the pyramidal cells located in deeper layers project up to the superficial layers of cortex and can contribute to the absorption of infrared energy. Astrocytes present another possible component underlying the INS-induced response. It has been suggested that astrocytes have a role in generating hemodynamic responses. Astrocytes have an active role in modulating neuronal transmission.

Certain aspects of the present disclosure are directed to applying INS to the cortex to evoke excitatory and/or inhibitory responses. In certain embodiments, the INS is configured and applied to the cortex to evoke responses of the cortex that have stable inhibitory effects for a predetermined time period. For example, the INS can be configured and applied to the cortex to inhibit neuronal activities of the cortex. In certain embodiments, the laser is of radiant exposure 0.055 J/cm$^2$, spot size 850 µm, repetition rate of 200 Hz, pulse width 250 µs, train length 500 ms. In certain embodiments, the INS is utilized to inhibit the neuronal activities of the cortex for about 1 and 2 seconds. Spot size typically refers to the diameter of light beam at the surface of the tissue.

INS can have a suppressive effect on apical pyramidal cell dendrites in the superficial layers. INS can also have an excitatory effect on inhibitory neurons in superficial layers, resulting in the suppressed pyramidal neuronal responses. Infrared laser can increase the GABA current in isolated single cell recordings using cultured rat neurons; INS can have direct effects on inhibitory neurons. It is likely that the predominant INS effect is preferential activation of inhibitory neurons. This is consistent with the effective penetration depth of the INS wavelength and stimulation parameters used here, which is likely to reach primarily layers I-II where inhibitory neurons are a predominant cellular component.

Certain aspects of the present disclosure are directed to the size (i.e. diameter) and numerical aperture (NA) of the laser stimulation fiber, the proximity of the fiber to the cortex, as well as the resulting activation spot on the cortex produced by the fiber. In certain embodiments, the optical fiber has a predetermined diameter and is position at a predetermined distance from the stimulation site such that the infrared laser delivered through the optical fiber covers a surface of the stimulation site entirely. In certain embodiments, the optical fiber can have a numerical aperture in a range of about 0.1 to about 0.4. In certain embodiments, the numerical aperture is about 0.22. In certain embodiments, the size of the activation spot is adjusted to vary the excitatory and inhibitory effects evoked and possibly their respective magnitudes. The large size of the activation spot may have the effect of recruiting additional inhibitory circuits in cortex, in particular somatosensory cortex. In certain embodiments, the optical fiber has a diameter in a range of about 5 µm to about 1000 µm. In certain embodiments, the covered surface of the stimulation site has a spot size in a range of about 5 µm to about 2 mm diameter. In certain embodiments, a fiber having a diameter about 400 µm can be positioned at distances up to about 1.1 mm from the cortex, resulting in a spot size of up to 800 µm. In certain embodiments, the fiber was placed between 0 and 1000 µm from cortex. Additional inhibitory circuits can be activated when the spot size goes beyond the receptive field size.

It is envisioned that INS can have many applications in the field of neuroscience, because of the benefits from the high spatial selectivity of INS. For instance, INS could be used to study functional neural circuitry. While electrical stimulation is an established stimulation method in the field of neuroscience [Fritsch and Hitzig, 1870]; [Galvani, 1791], inherent electrical field spread makes it difficult to contain the area of neural activation. Infrared energy is governed by its optical penetration depth and can be engineered to target a specific volume of tissue. Consequently, neural activation by INS has been shown to be more spatially precise than electrical stimulation [Wells et al., 2005a,b] and has the potential to stimulate a single neuron [Feng et al., 2010]. Infrared neural stimulation also has the advantage of being minimally invasive, reducing the risk of damaging neural tissue by physical contact, and could be a useful high spatial resolution brain mapping method during intraoperative procedures during neurosurgery [Roux and Tremoulet, 2002]; [Starr et al., 2002]. INS can also potentially be applied for deep brain stimulation.

Certain aspects of the present disclosure show that INS can be used to produce intrinsic optical images of the intact rat brain in response to INS that follow established time courses for intrinsic responses to tactile stimulation of the forepaw and whisker. Single unit recordings made in regions of activation identified by optical imaging indicate inhibition during INS whereas tactile stimulation induced excitatory responses. To further our understanding of INS induced signals in the cortex, optical imaging can be used to assess calcium dynamics during INS. Infrared neural stimulation and electrical stimulation (ES) can be performed in rat somatosensory cortex corresponding to the forepaw, hindpaw, and barrel field cortex. A craniotomy and durotomy can be performed over somatosensory cortex, and Oregon green calcium dye (BAPTA 488, Invitrogen) can be injected into somatosensory cortex with a picospritzer. A pulsed diode laser (Lockheed Martin Aculight, Bothel Wash.) can be used to perform INS in somatosensory cortex. In certain embodiments, INS can be performed at a wave length of about 1.875 µm and 1.94 µm using repetition rates between 10-250 Hz for pulse trains ranging between 500 ms to 1000 ms. In certain embodiments, electrical stimulation (3 Hz for 3 sec) can be applied to the hindpaw or forepaw of the animal through needle electrodes to identify regions of cortex corresponding to the stimulated limb. Electrical stimulation parameters were adjusted to induce a small twitch in the stimulated paw. In certain embodiments, calcium transients evoked by INS can be studied by varying the radiant exposure (stimulus amplitude), laser pulse repetition rate, laser wavelength, laser pulse width, and pulse train length. In certain embodiments, optical images can be collected at 30 Hz for 30 secs under 470 nm (Calcium dye) illumination. In certain embodiments, optical images can be collected at 90 Hz (30 Hz for each wavelength of light) for 30 secs under 470 nm (Calcium dye), 530 nm (total Hb), and 632 nm (deoxy Hb) illumination. The resulting images can be compared for signal amplitude, spatial precision, and temporal precision between different laser parameters and similar electrical stimulation parameters.

IMPLEMENTATIONS AND EXAMPLES

Without intent to limit the scope of the invention, exemplary methods and their related results according to the embodiments of the present disclosure are described below. Note that titles or subtitles may be used in the examples for convenience of a reader, which in no way should limit the scope of the invention. Moreover, certain theories are proposed and disclosed herein; however, in no way they, whether they are right or wrong, should limit the scope of the present disclosure so long as the present disclosure is practiced according to the description without regard for any particular theory or scheme of action.

Example 1

In this example, infrared neural stimulation (INS) can be used to evoke responses in the central nervous system of mice, rats, and non-human primates in response to pulsed infrared light. Specifically, among other things, pulsed infrared light evokes an intrinsic (hemodynamic) optical signal which is similar to intrinsic signals evoked by natural and electrical stimulation in rat somatosensory cortex. The intrinsic optical signal (IOS) strength can be increased with increasing repetition rate and radiant exposures. Intrinsic optical imaging also indicate spatial precision by only activating a region of cortex approximately 1 mm in diameter at the peak of the signal. Electrophysiological recordings in rat somatosensory cortex exhibiting evoked intrinsic signals indicate a period of inhibition during INS without functional loss or damage to stimulated tissue. The recordings are stable over time. Additionally, the electrophysiological recordings indicate that the evoked hemodynamic signal is the result of a complex physiological process and not just vasodilation due to heat associated with the laser.

The inventive discovery has been further confirmed in fluorescent calcium dye imaging in rat somatosensory cortex using Oregon Green Calcium dye injected into cortex. The calcium dye only fluoresces to an increase of intracellular calcium which removes the possible vasodilation component associated with intrinsic optical imaging. Pulsed infrared light was used to evoke calcium waves associated with the laser in rat somatosensory cortex. The laser evoked calcium wave exhibits two components which are similar to calcium waves observed for neural and astrocytic calcium waves, suggesting that pulsed infrared light can be used to activate both neurons and astrocytes in cortical tissue. Parametric studies revealed the same trends observed for increasing radiant exposure and repetition rates in the intrinsic optical imaging study discussed previously. The calcium wave strength also increased in response to increased stimulation durations.

The above discoveries have been further supported by work performed in embodiments related to the mouse cerebellum using flavoprotein and calcium dye imaging. Preliminary results support the finding that pulsed infrared light inhibits neuronal activity where after laser irradiation the flavoprotein response to electrical stimulation is diminished. Pharmacological studies revealed that blocking the inhibitory neurotransmitter GABA increased the intrinsic fluorescence in the cerebellum suggesting an excitatory component to the laser stimulus. Application of an astrocytic poison greatly diminished the flavoprotein signal during laser stimulation further supporting the other studies hypothesis that the laser activates an astrocytic response. However, during calcium dye imaging the astrocytic poison had no statistically significant effect on the calcium wave during laser stimulation suggesting the presence of neuronal response.

These techniques can be translated to non-human primates for stimulating somatosensory and visual cortex. Preliminary results indicate both excitatory and inhibitory response to INS. Intrinsic optical imaging has been used to identify regions of activation at the stimulus location as well as a projection area associated with the stimulated location of cortex. Electrophysiology has been used to record both excitatory and inhibitory responses in multiple animals. Specifically in visual cortex, where neurons are highly organized, the pulsed infrared light has been shown to modulate the intrinsic optical response to visual stimulation for an individual eye suggesting INS can be used for functional stimulation.

According to the various embodiments of the present disclosure, INS can be applied to the central nervous system. Pulsed infrared light can evoke optical signals throughout cortical structures in both the cerebrum and cerebellum. INS was discovered and observed, by practicing certain aspects of present disclosure, to evoke an inhibitory response that was measured using traditional electrophysiological methods. Results have indicated that pulsed infrared light can be used to activate both neurons and astrocytes in the CNS. These results have been confirmed across multiple studies using mice, rats, and non-human primates. The impact of this invention, among other things, could lead to advancements in areas of neuroscience where selective inhibition is needed. One such area is deep brain stimulation where large active lesions, due to inherent current spread, can cause side effects for patients which are uncomfortable. INS in deep brain stimulation applications could inhibit the area of interest with a smaller footprint since the pulsed infrared light does not suffer from current spread associated with electrical stimulation. This application of INS to the CNS provides a new tool for neuroscientist to better understand how our nervous system works. The implication of astrocytes responding to pulsed infrared light makes INS a new methodology for neuroscientist to study the function and purpose of astrocytes in our nervous system. Electrical stimulation cannot be used evoke inhibitory responses locally; however INS has been shown in the studies discussed here to inhibit neural activity locally. The need for such a stimulus is illustrated by recent advances in optogenetics where neurons have been engineered to produce an opsin that produces an inhibitory response on a neuron. Infrared neural stimulation is intrinsic and does not require genetic manipulation to produce a response making it more likely to translate to clinical use in neurosurgery. The translation of INS to clinical use is supported by our work in primates where preliminary results have indicated both inhibitory and excitatory responses.

To approach in vivo cortical application, it is first investigated feasibility of CNS stimulation with infrared light by applying INS to thalamocortical brain slices in vitro [Cayce et al., 2010]. The thalamocortical brain slice model preserves a three-neuron network between cortical and thalamic neurons present in vivo [Agmon and Connors, 1991]; [Blanton et al., 1989]; [Kao and Coulter, 1997]. In the slice study, it is demonstrated that pulsed infrared light could stimulate CNS neurons and evoked potentials could be blocked with tetrodotoxin (TTX). Parametric studies showed that the absorption coefficient of a given wavelength determined stimulation threshold. An increase in spot size and higher repetition rates both reduced stimulation threshold. A temperature gradient (dT/dz or dT/dt) can be the mechanism by which pulsed infrared light induces neural activation [Wells et al., 2007a]. While the brain slice model was ideal for establishing feasibility, there are fundamental differences between an in vitro brain-slice and an in vivo application.

Pulsed infrared light can be used to regulate cortical neuronal activity in vivo and to investigate laser parameters that activated cortex without causing damage. Both electrophysiological and intrinsic optical imaging techniques were used to characterize signals generated by INS. Because intrinsic optical imaging offers a large field of view (~10 mm) and high spatial resolution (10 µm), it has been an effective way to examine functional organization in cerebral cortex and to guide microelectrode placement to characterize neuronal responses [Hillman, 2007]; [Roe, 2007].

In this example, rat somatosensory cortex corresponding to the forepaw and barrel fields is chosen, because these areas have been well characterized [Chapin and Lin, 1984; Dunn et al., 2005; Petersen, 2007; Tsytsarev et al., 2010] and lend themselves well to assessment of INS effects. It is discovered that INS can manipulate somatosensory cortex activity without apparent detriment to cortical function. INS is successfully applied to cortical structures in vivo. INS has clinical use and can be a useful tool for studies of neuronal circuitry.

Surgical Procedures

Briefly, male Long Evan rats (n=15; 300-500 g) were anesthetized with a 50% urethane (Sigma, St. Louis, Mo.) solution (I.P. 1.4 g/kg). The toe-pinch test was used to ensure the animal was in an adequate state of anesthesia. A tracheotomy was performed to allow for ventilation (Harvard Model 683 Small Animal Ventilator, Harvard Apparatus Holliston, Mass.) of the animal during the experiment. The animal was placed in a stereotactic frame and a craniotomy and durotomy were conducted to expose somatosensory cortex (+2 to −5 mm AP, and 7 mm lateral to bregma) (Chapin and Lin, 1984; Paxinos and Watson, 2007). Mannitol 1.0 ml, 20% concentration) was given I.P. to prevent potential brain swelling. Warm (~37° C.) 3% agar (Sigma, St. Louis, Mo.) in saline was used to stabilize the cortex and a glass coverslip was placed on the agar to create an imaging window for optical imaging. A small portion of agar was dissected away to create an access port for placement of the optical fiber for application of INS.

Optical Imaging

In certain embodiments, ten animals can be used in experiments involving optical imaging. Intrinsic signal optical imaging was performed using a CCD camera (e.g., NEUROCCD-SM256, SciMeasure Analytical Systems, Inc. Decatur, Ga.) positioned over the craniotomy. Cortex was illuminated by 632 nm bandpass filtered light from a halogen light source and focused onto the brain using fiber optics. Light reflected from cortex was collected onto the CCD chip using a 50 mmF/1.3 lens (e.g., DARK INVADER, B.E. Meyers & Co., Inc., Redmond Wash.) and a lens extender (e.g. 2×) for C mount security cameras such as Ex2C COMPUTAR C-mount extender (CBC (AMERICA) Corp., Commack, N.Y.) to provide a working distance of 20 cm and a FOV of approximately 5×5 mm. This working distance allowed for easy placement of the optical fiber used for laser stimulation.

An imaging system such as the REDSHIRT Imaging System running CORTIPLEX software (Redshirt Imaging, Decatur, Ga.) can control the sequence of the entire experiment. The imaging system can collect images from the CCD camera and controlled the stimulus presentation.

FIG. 1 shows an experimental setup for infrared neural stimulation and optical imaging. FIG. 1A is a schematic diagram of the experimental setup. Experiment is controlled by imaging software 102 that acquires images from the CCD camera 104 and determines when stimuli are presented by signaling a separate computer 106 running control software that is responsible for stimulus presentation. The control computer 106 triggers stimuli by sending TTL pulses to either the piezoelectric controller 114 or the laser generator 110. The optical fiber 118 used to deliver infrared light is positioned on cortex or just above cortex through a window created through agar and the piezoelectric bender 122 is positioned on targeted forepaw digit or whiskers 126. FIG. 1A shows an example of a fiber positioned on cortex through a port created in the agar.

Figure 1B:
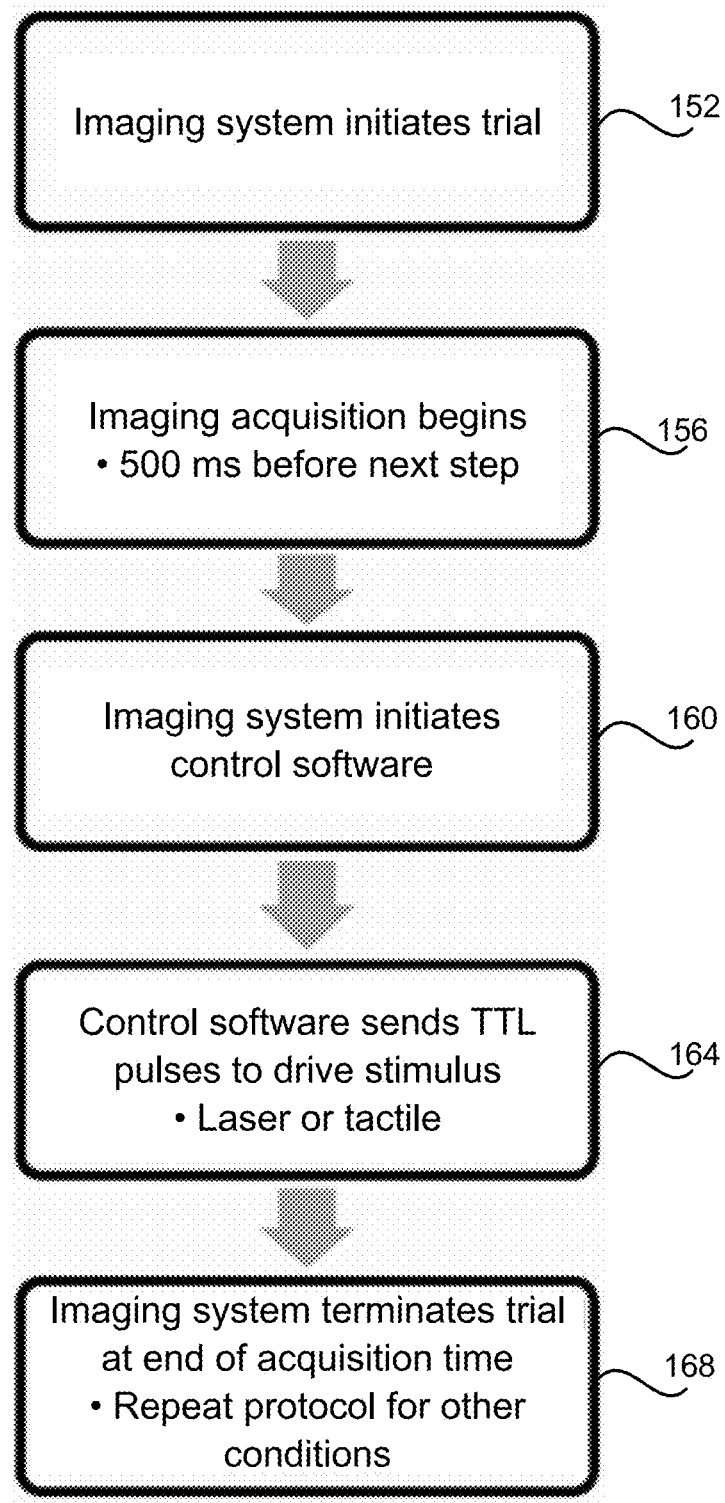
FIG. 1B shows an imaging protocol flow chart of one trial for a given condition in accordance with certain embodiments of the present disclosure.

FIG. 1B shows an imaging protocol flow chart of one trial for a given condition. At operation 152, the imaging system 102 (e.g., the REDSHIRT Imaging System) initiates the trial. At operation 156, the imaging system 102 starts collecting image frames at a predetermined time (e.g., 500 ms) before the next step. At operation 160, the imaging system 102 initiates a control software 106, e.g., sends a binary code specifying a stimulus condition to a stimulus computer running LABVIEW software and National Instruments hardware (National Instruments, Austin, Tex.). At operation 164, the control software 106 sends pulses to drive stimulus. For example, the LABVIEW program sends TTL pulses to the laser generator 110 and the driver 114 of the piezoelectric stimulators at the desired repetition rate for a given experiment. Radiant exposure, pulse width, and wavelength can be all preset on the laser. Voltage and pulse width can be preset on the piezoelectric controller 114. Stimuli can be presented 300 ms after trial onset. At operation 168, the imaging system 102 terminates the trial at the end of acquisition time. After image acquisition, the intertrial interval can be 8-15 s. The above imaging protocol can be repeated for other conditions.

There can be at least two types of imaging runs. For runs with only cutaneous stimulation, images can be typically collected for 3 s at a frame rate of 5 Hz. For experiments with at least one INS condition, images can be collected for 10 to 15 s at a frame rate of 10 Hz. In all experiments there can be at least two conditions for a given imaging run: one stimulus condition (i.e. tactile or INS) and one blank (no stim) condition. In most cases there were multiple stimulation conditions (i.e. one tactile and 3 laser conditions). Conditions were grouped into blocks where each condition was presented in an interleaved and pseudorandom manner. Between 25 and 50 blocks of each condition were collected for one imaging run.

Laser Stimulation Parameters

Wavelength selection for performing infrared neural stimulation can be based on the optical penetration depth of light in tissue which was estimated using absorption data for water since biological soft tissue is 70% water [Hale and Querry, 1973]. Studies using infrared light to stimulate tissue have indicated that an optical penetration depth of 300-600 µm can be optimal for stimulating neural tissue [Cayce et al., 2010; Richter et al., 2010; Wells et al., 2005a]. This optical penetration depth range can correspond to a wavelength of 1.875 µm. Infrared neural stimulation can be performed using a 1.875 µm±0.02 µm CAPELLA neural stimulator (Lockheed Martin Aculight, Bothel, Wash.). Light was delivered to the cortex through a 400 µm OCEAN OPTICS fiber (St. Petersburg, Fla.) with a numerical aperture (NA) of 0.22. The fiber was placed between 0 and 1000 µm from cortex using a hydraulic micromanipulator (Narishige, Tokyo, Japan). Laser repetition rate can range between 50 and 200 Hz, and pulse width can be held constant at 250 µs. The average power from the laser was measured at the fiber tip using a POWERMAX 500D laser power meter with a PM3 detector head (Coherent, Santa Clara, Calif.). Radiant exposure can be calculated based on the NA of the fiber and the distance of the fiber tip from cortex [Wells et al., 2005a]. The radiant exposure varied between 0.01 and 0.55 J/cm$^2$ and was dependent on the stimulation parameters used for a given experiment. Pulse train duration for all INS experiments can be 500 ms. Laser triggering can be controlled via a LABVIEW software interface (FIG. 1).

Tactile Stimulation Parameters

Piezoelectric benders (Noliac, Kvistgaard, Denmark) can be used to present vibratory stimuli to the forepaw digits or the whiskers contralateral to the cortical recording site. Each piezoelectric stimulator can be driven using DC pulses from a stimulator such as GRASS stimulator (S88 Astro-Med Inc., West Warwick, R.I.) that is triggered by the control software (e.g., LabVIEW software) to control stimulation (FIG. 1). For optical imaging, square wave pulses at 8 Hz for 3 s are delivered to the piezoelectric; for electrophysiology, pulses are delivered to the piezoelectric at 1 Hz for 3 s. Neurophysiological responses to palpation are used to map somatosensory cortex and to assess the health and functionality of cortex before, during and after INS presentation.

Optical Imaging Data Analysis

Analysis of optical imaging data can be performed with software such as that written in MATLAB (Mathworks, Natick, Mass.). All conditions (blank and experimental) can be first frame subtracted and then summed across trials to maximize signal to noise ratio. Experimental conditions can be then blank-subtracted to measure changes in the intrinsic signal from baseline [Roe, 2007]. Trial by trial assessment of image quality can be conducted to remove any bad trials due to lighting abnormalities, large physiological movement, or camera acquisition errors. As determined by the signal to noise ratio for a given experiment, image maps can be optimized for display by clipping the range (0.8-2.5 standard deviations) of pixel values around the mean. In some cases, a blood vessel mask can be used to reduce artifact signal related to surface vasculature. Standard Gaussian low-pass and median high-pass filtering can be used to remove contamination from uneven illumination and from other physiological noise sources. Stimulation conditions can be compared to blank conditions to identify significant pixels and create t-maps. This analysis aided in identifying regions of interest for time course analysis. The time course of the intrinsic signal can be examined at selected sites by averaging the values of pixels within the region of interest. The summed pixel value from the first image frame can be subtracted from each subsequent sequence of frames in a condition's sequence and then used as a divisor to measure the change in reflectance over background reflectance (dR/R).

The blank time course can be then subtracted from each experimental condition to remove non-stimulus associated changes in reflectance. In a given experiment, the maximum deflection magnitude of the signal can be used to determine the peak of the intrinsic response and was used to compare the ability of each stimulation condition to induce intrinsic responses.

Electrophysiology Recordings

Single unit electrophysiology can be used to assess the cortical neuronal responsiveness before, during, and after INS. Tungsten microelectrodes (1-3 MΩ, World Precision Instruments, Sarasota, Fla.) can be inserted into cortex at depths of 50-500 μm in regions of interest identified from piezoelectric tactile stimulation. Single units can be isolated with high spontaneous activity to study the effects of INS on neuronal activity. The optical fiber can be placed approximately 1 mm away from the electrode. Signals can be filtered and digitized using a 16 channel AM-Systems (e.g., Sequim, Wash.) differential amplifier using a 300-5 K bandpass filter. The control software such as LABVIEW interface can be used to control presentation of tactile and laser stimulation, and data collection software such as DATAWAVE software (Loveland, Colo.) can be used to collect single unit data. Peristimulus time histograms (PSTH) can be generated using DATAVIEW software. A paired t-test analysis can be used to determine the significance of changes observed in the PSTH related to laser stimulation.

Results

The description below shows that experiments can be conducted in cortex such as rat somatosensory cortex, either in barrel cortex in response to whisker stimulation or in forepaw cortex in response to tactile stimulation of the digits.

Intrinsic Optical Imaging of Vibrotactile Stimulation

Baseline functionality and viability of somatosensory cortex prior to the application of INS can be assessed through optical imaging of hemodynamic responses in somatosensory cortex.

Figure 2:
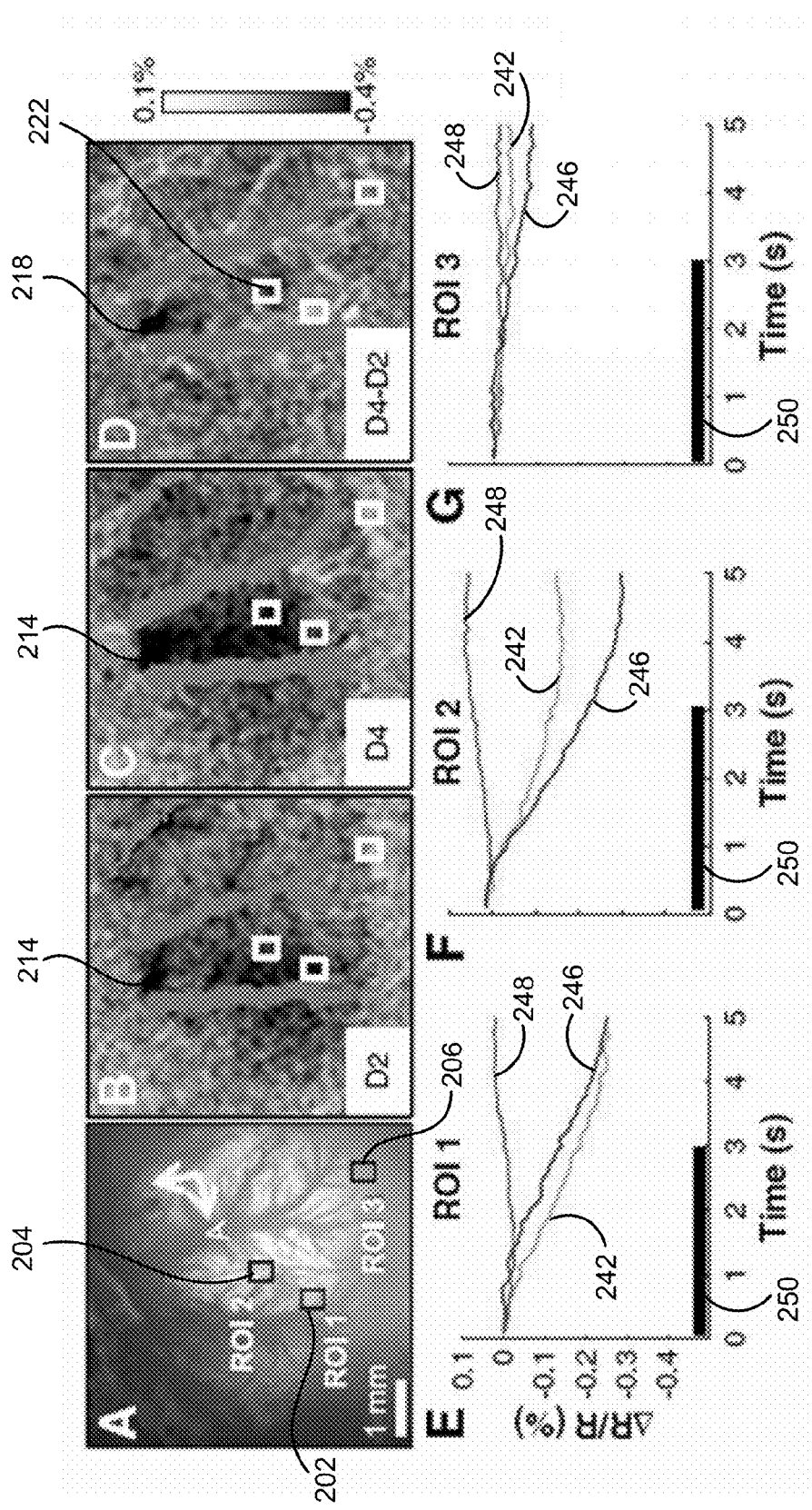
FIG. 2 illustrates a typical intrinsic imaging response to vibrotactile stimulation of contralateral forepaw digits in accordance with certain embodiments of the present disclosure.

FIG. 2. illustrates typical intrinsic imaging response to vibrotactile stimulation of contralateral forepaw digits. FIG. 2A shows a blood vessel map. Black boxes 202, 204, 206 are region of interests (ROIs) where time course data was calculated for D2, D4, and no stimulation conditions. FIGS. 2B and C show activation maps in response to stimulation of D2 and D4 respectively. Darkening 214 in image indicates activation. FIG. 2D shows a D4-D2 subtraction map; darkened area 218 represents selective D4 and lightened area 222 represents selective D2 activation. FIGS. 2E-G show time courses of intrinsic signals taken from region of interests demarcated by black and white boxes 202, 204, 206 in FIGS. 2A-D. Three traces 242, 246, 248 indicate responses to D2, D4, and no stimulation conditions, respectively. ROI 1 202 corresponds to a D2 region of cortex, ROI 2 204 corresponds to a D4 region of cortex and ROI 3 206 corresponds to a non-activated region of cortex. Black bar 250 represents the timing of the stimulus. Stimulation parameters are 3 second train at 8 Hz. Imaging parameters are 10 fps and 21 trials. "A" in the drawing indicates anterior; "M" indicates medial. Scale bar next to FIG. 2D indicates clipping range of % change in signal in respective images.

FIG. 2 illustrates a normal functional response to vibrotactile stimulation of D2 and D4 of the contralateral forepaw in response to taps delivered by a piezoelectric stimulator (8 Hz, 3 s). Darker pixels in the functional maps indicate activation (FIGS. 2B, C, and D). Cortical activation to D4 stimulation was medial and posterior to D2 as emphasized by the dark (D4, ROI 2) and light (D2, ROI 1) ROIs in the subtraction map between the two conditions (FIG. 2D). FIGS. 2E, F and G illustrate signal time courses taken from the D2 (ROI 1), D4 (ROI 2), and control (edge of craniotomy, ROI 3) locations, respectively. Optical responses to D2 stimulation, D4 stimulation, and the no stimulation conditions are plotted in traces 242, 246, 248, respectively. As indicated by the larger negative deflections in intrinsic signal magnitude, the time courses of activation (FIGS. 2E-G) demonstrate preferential activation for stimulation of D2 at the D2 site (ROI 1) and for stimulation of D4 at the D4 site (ROI 2). The intrinsic signals were not focal within the forepaw representation as D2 stimulation activated the D4 ROI and D4 stimulation activated the D2 ROI. The blank condition (no stimulation) produced little response at the D2 and D4 sites, which was comparable to the lack of signal obtained at the control site for all three conditions (FIG. 2G). These activation maps are representative of the optical responses obtained in rat barrel cortex and rat forepaw cortex generated by tactile stimulation in our experiments.

Demonstration of INS Induced Optical Intrinsic Signals

Infrared neural stimulation can then be examined to determine if pulsed infrared light could induce an optical response in cerebral cortex comparable to that induced by natural sensory stimulation.

Figure 3:
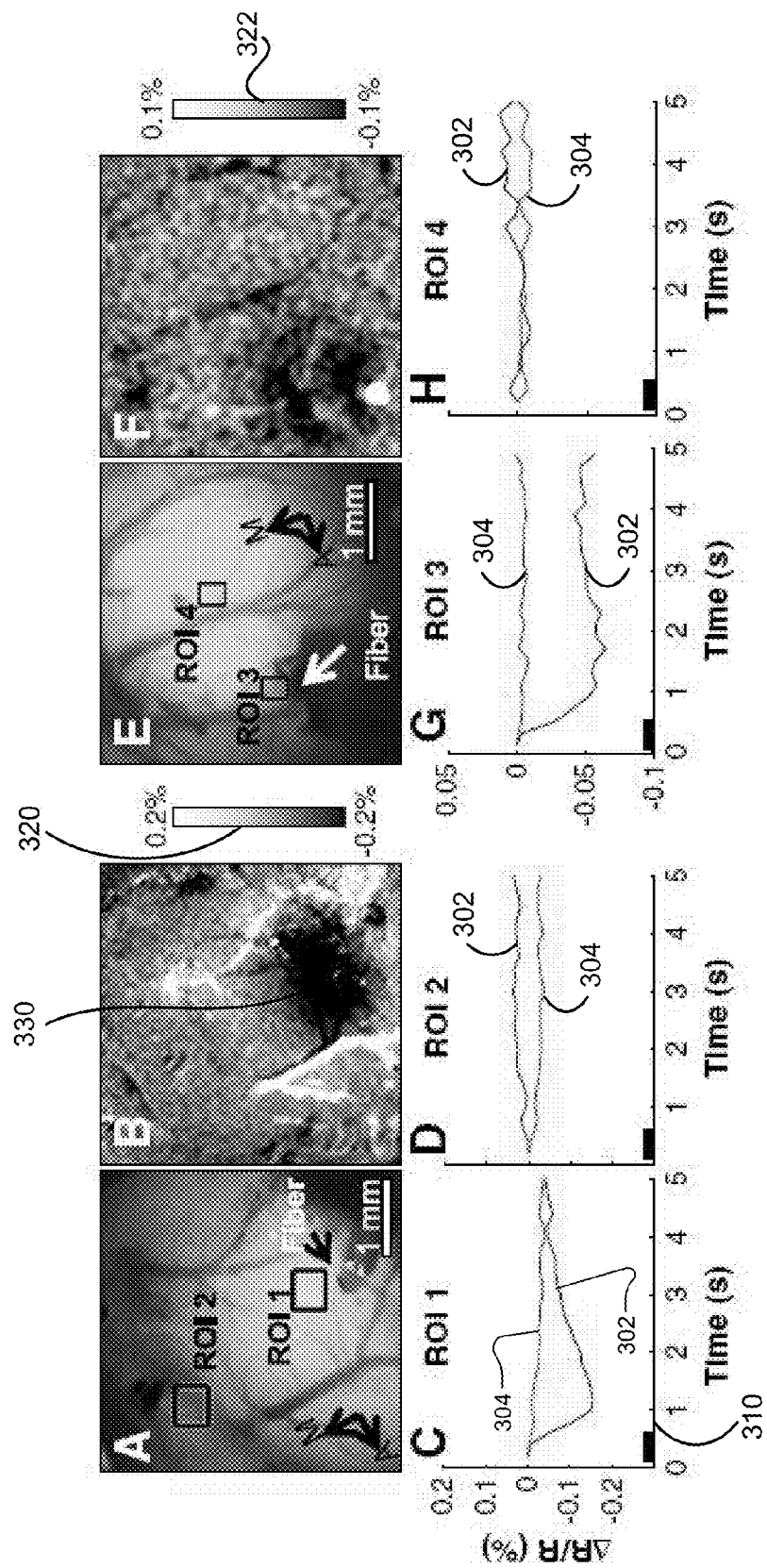
FIG. 3 illustrates INS evoked intrinsic optical signals in somatosensory cortex in accordance with certain embodiments of the present disclosure.

FIG. 3 illustrates INS evoked intrinsic optical signals in somatosensory cortex. INS evokes intrinsic optical signals in somatosensory barrel field (FIGS. 3A-D) and forepaw cortex (FIGS. 3E-H) in separate experiments (632 nm). FIGS. 3A and 3E illustrates blood vessel maps indicating ROI locations and fiber location (Fiber). ROI 1 and 3 are sites near INS stimulation; ROI 2 and 4 are sites distant from INS stimulations. FIGS. 3B and 3F illustrate activation maps obtained to laser stimulation in barrel field cortex (FIG. 3B) and forepaw cortex (FIG. 3F). FIGS. 3C and 3G illustrates time course of signals in region near laser stimulation (ROI 1 and ROI 3). FIGS. 3D and 3H illustrates time courses of signals distant from laser stimulation site (ROI 2 and ROI 4). Line 302 reflects signal evoked by laser stimulation. Line 304 shows control (no stim) time course. There is no appreciable optical response at this distance from laser stimulation. Laser parameters are: $\lambda$=1.875 μm, repetition rate=100 Hz, pulse train duration=500 ms, pulse width=250 μs, radiant exposure=0.55 J/cm2, and spot size diameter=400 μm. Imaging parameters are: 5 fps, ITI=8 s, and Trials=40. "A" in the drawing indicates anterior; "M" indicates medial. Black bar 310 in FIGS. 3C-3H represents the timing of the stimulus. Scale bars 320, 322 next to FIGS. 2B and 2F indicate clipping range of respective images.

FIG. 3 demonstrates that INS of cortical tissue can induce changes in optical reflectance signal of somatosensory cortex. A optical fiber is placed over somatosensory cortex corresponding to the barrel fields (FIG. 3A). Stimulation of the cortex with INS (e.g., 100 Hz, 0.55 J/cm2, $\lambda$=1.875 μm, 250 μs pulse width, 500 ms pulse train) can evoke changes in optical reflectance at and near the optical fiber location, as illustrated by the activation map shown in FIG. 3B. The activated region of cortex 330 (dark pixels) in response to these INS parameters can produce a focal region of activation, approximately 1.5-2 mm in diameter. As shown in FIG. 3C, the time course reaches a peak after 1 s and has a duration of 3 s. The magnitude of the change in reflectance peaks at approximately 0.15%. No such optical reflectance change was obtained during the Blank condition. Optical signal changes are not observed at sites distant from the INS location (FIG. 3D), indicating that the INS-induced signal has high spatial selectivity. In a separate experiment, the same laser conditions used in FIG. 3A are used to generate a response in forepaw cortex to demonstrate that INS can evoke optical responses in different cortical areas (FIGS. 3E-H). These experiments demonstrate that INS is capable of inducing optical responses in somatosensory cortex, some of which are similar to those obtained with natural tactile stimulation.

Effects of Laser Repetition Rate on INS Evoked Intrinsic Signal

To further establish that the optical signal was indeed induced by INS, repetition rate can be varied to study how the reflectance signal changed in relation to the repetition rate of the laser.

FIG. 4 illustrates intrinsic signals produced by different rates of INS. FIG. 4A shows a blood vessel map. Location of the optical fiber is indicated by arrow 402. Pixels 406 indicate significant pixels in t-test between 100 Hz stimulation and blank condition. FIGS. 4B-E show activation maps of laser repetition rates: 50 Hz in FIG. 4B, 100 Hz in FIG. 4C, 150 Hz in FIG. 4D, and 200 Hz in FIG. 4E. FIG. 4F show time course of response 410, 412, 414, 416, 418 resulting from laser stimulation conditions 50 Hz, 100 Hz, 150 Hz, and 200 Hz and blank conditions, respectively. FIG. 4G shows a relationship of laser repetition rate and the peak amplitude of the intrinsic signal, which fit with an exponential equation. Laser parameters are: $\lambda$=1.875 μm, repetition rates=50, 100, 150, 200 Hz, pulse train duration=500 ms, pulse width=250 μs, radiant exposure=0.55 J/cm2, spot size=400 μm. Imaging parameters are: 40 Trials, 5 f/s. A=anterior, M=medial. Black bar 422 in FIG. 4F represents the timing of the stimulus. Scale bar 426 next to FIG. 4E indicates clipping range of images 4B-E.

It is demonstrated that the greater the total light energy applied to the cortex, the stronger the optical reflectance change. Using a 500 ms duration pulse train and 250 μs pulse width, repetition rates of 50, 100, 150, and 200 Hz (FIGS. 4B-E) are applied. FIG. 4A illustrates the location of the optical fiber 402 (Fiber) as well as a t-map generated via pixel-by-pixel t-tests (p<0.001) between the 100 Hz laser stimulation and blank conditions (pixels 406). As can be seen qualitatively in FIG. 4B-E, an increase in laser repetition rate increases the size of the activation region. Quantitatively, the 200 Hz laser stimulus 416 produces the largest optical reflectance change, while a 50 Hz stimulus 410 produces the smallest response (FIG. 4F). As shown in FIG. 4G, the magnitude of the intrinsic signal exhibits an exponential fit with repetition rate [cf. Cayce et al., 2010].

Effects of Radiant Exposure on Intrinsic Signal

Threshold is an important aspect of INS to consider when developing the modality as an alternative to electrical stimulation. FIG. 5. shows that increased INS radiant exposure leads to an increase in intrinsic signal magnitude. FIG. 5A illustrates a blood vessel map showing location of ROI 502 and fiber location 506. FIGS. 5B and C illustrates activation maps from stimulation with 0.14 J/cm$^2$ and 0.48 J/cm$^2$. FIG. 5D illustrates time courses of signals for different radiant exposures. FIG. 5E illustrates a relationship of radiant exposure and peak amplitude of the intrinsic signal, which fit with a linear equation. Laser parameters are: $\lambda$=1.875 μm, repetition rate=200 Hz, pulse train duration=500 ms, pulse width=250 μs, spot size=400 μm. In FIG. 5D, line 520 indicates radiant 0.14 J/cm$^2$, line 522 indicates 0.21 J/cm$^2$, line 524 indicates 0.32 J/cm$^2$, line 526 indicates 0.37 J/cm$^2$, and line 528 indicates 0.48 J/cm$^2$. "A" in the drawing indicates anterior; "M" indicates medial. Black bar 540 in FIG. 5D represents the timing of the stimulus. Scale bar 544 next to FIG. 5C indicates clipping range of images.

FIG. 5 displays the functional response when the radiant exposure of each pulse is adjusted across imaging runs, and examines the time course of activation for the ROI 502 shown in FIG. 5A. The laser parameters of stimulation used to generate these time courses are 200 Hz, 500 ms duration pulse train of 250 μs pulses at the five different radiant exposures. FIGS. 5B and C show the functional maps to 0.14 J/cm$^2$ and 0.48 J/cm$^2$ radiant exposures. The smallest radiant exposure (0.14 J/cm$^2$; FIG. 5D, line 520) resulted in the smallest intrinsic signal magnitude. Intermediate radiant exposures (0.21 J/cm$^2$ and 0.32 J/cm$^2$; lines 522, 524) produce intermediate signal size, and the largest radiant exposures tested (0.37 J/cm$^2$ and 0.48 J/cm$^2$; lines 526, 528) resulted in the largest signal amplitudes. The magnitude of the intrinsic signal exhibits a linear fit with radiant exposure (FIG. 5E). The area of activation also increased with radiant exposure energy, as shown qualitatively (FIGS. 5B and C).

Thus, within the ranges tested, both increases in laser stimulation rate and radiant exposures resulted in greater optical activation signal, suggesting a consistent and specific effect of laser stimulation on cortical response.

Effective Distance of INS Induced Effect

The spatial selectivity of INS in cortical tissue is characterized by calculating the time course of the intrinsic signal at five distinct locations.

Figure 6:
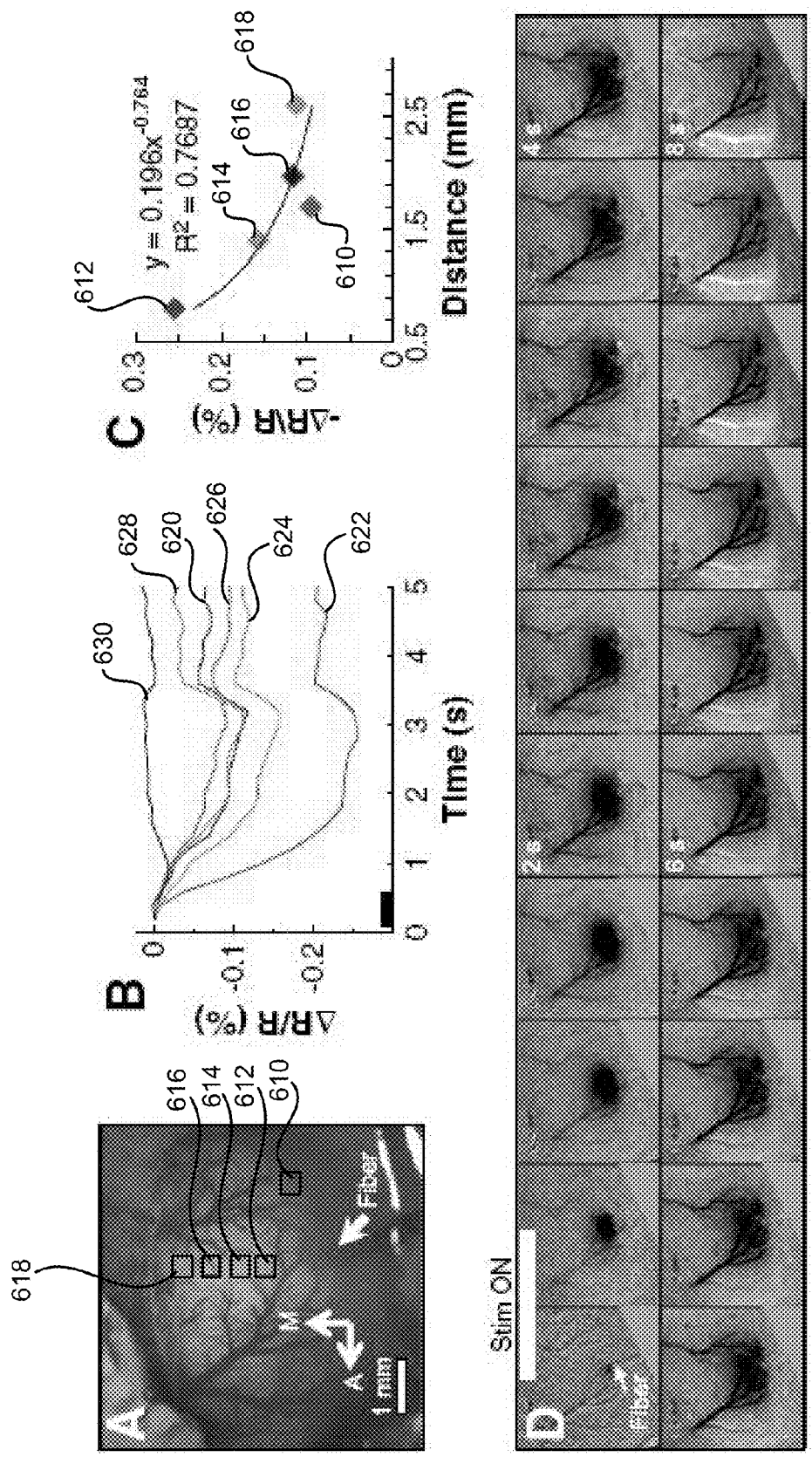
FIG. 6 illustrates spatial distribution of intrinsic signals in response to INS in accordance with certain embodiments of the present disclosure.

FIG. 6 illustrates spatial distribution of intrinsic signal in response to INS. FIG. 6A shows a blood vessel map with sampled ROIs overlaid. Boxes 610, 612, 614, 616, 618 in map correspond to time course traces 620, 622, 624, 626, 628 respectively, displayed in FIG. 6B. FIG. 6B shows intrinsic signal time courses at different distances from the INS stimulation location. Line 630 corresponds to the no stimulation condition collected from the ROI 612. FIG. 6C shows peak amplitude of the intrinsic signal as a function of distance from the fiber. Relationship fit with an exponential equation. FIG. 6D shows time mosaic of optical images to illustrate the spatiotemporal aspects of the INS induced intrinsic signal. Images are temporally binned by two decreasing the effective frames per second to 2.5 Hz. Laser parameters are: $\lambda=1.875$ μm, repetition rate: 200 Hz, pulse train duration=500 ms, pulse width=250 μs, radiant exposure=0.55 J/cm$^2$, spot size=400 μm. Imaging parameters are: 40 trials, 5 f/s. Black bar in (B) represents the timing of the stimulus. "A" in the drawing indicates anterior; "M" indicates medial.

FIG. 6 displays the time courses based on distance from the laser stimulation site (200 Hz, 0.55 J/cm2, pulse width 250 μs, pulse train 500 ms). In FIG. 6A, the box 612 represents the region of interest closest to the optical fiber; the boxes 616, 618 are the most distant regions of interest. The peak signal is largest for the location closest to the optical fiber (FIG. 6B, line 622) and decreases in amplitude with distance from the stimulation location. This decline in signal size with distance also occurred in other directions as indicated by the comparable signal amplitude of ROIs 616, 618 in FIG. 6A. As also shown in FIG. 3, in certain embodiments, the prominent effects of INS stimulation lie within 1-2 mm of the stimulation site and decline rapidly as a function of distance from the stimulation site (FIG. 6C). The spatial temporal aspects of the signal are illustrated in FIG. 6D through a time series of optical images taken during the imaging run. The data is temporally binned by 2 to decrease the number of images displayed in the mosaic; therefore, each frame represents 400 ms in time. The stimulus comes on at 200 ms and is off at 700 ms after trial start, which indicates frames 1-2 represent the time the laser was turned on. The signal peaks between frames 7 and 8 which corresponds to the time courses are displayed in FIG. 6B. Furthermore, FIG. 6D demonstrates that laser induced intrinsic signal is focal in an area measuring approximately 1 mm in diameter at its peak demonstrating the spatial precision of INS. This spatially limited characteristic makes INS a potentially useful method for studies requiring focal stimulation. The time series of images for 50, 100, 150, and 200 Hz are included as a supplemental figure to further demonstrate the effects of repetition rate on the evoked signal and to demonstrate the spatial precision of INS.

Figure 7:
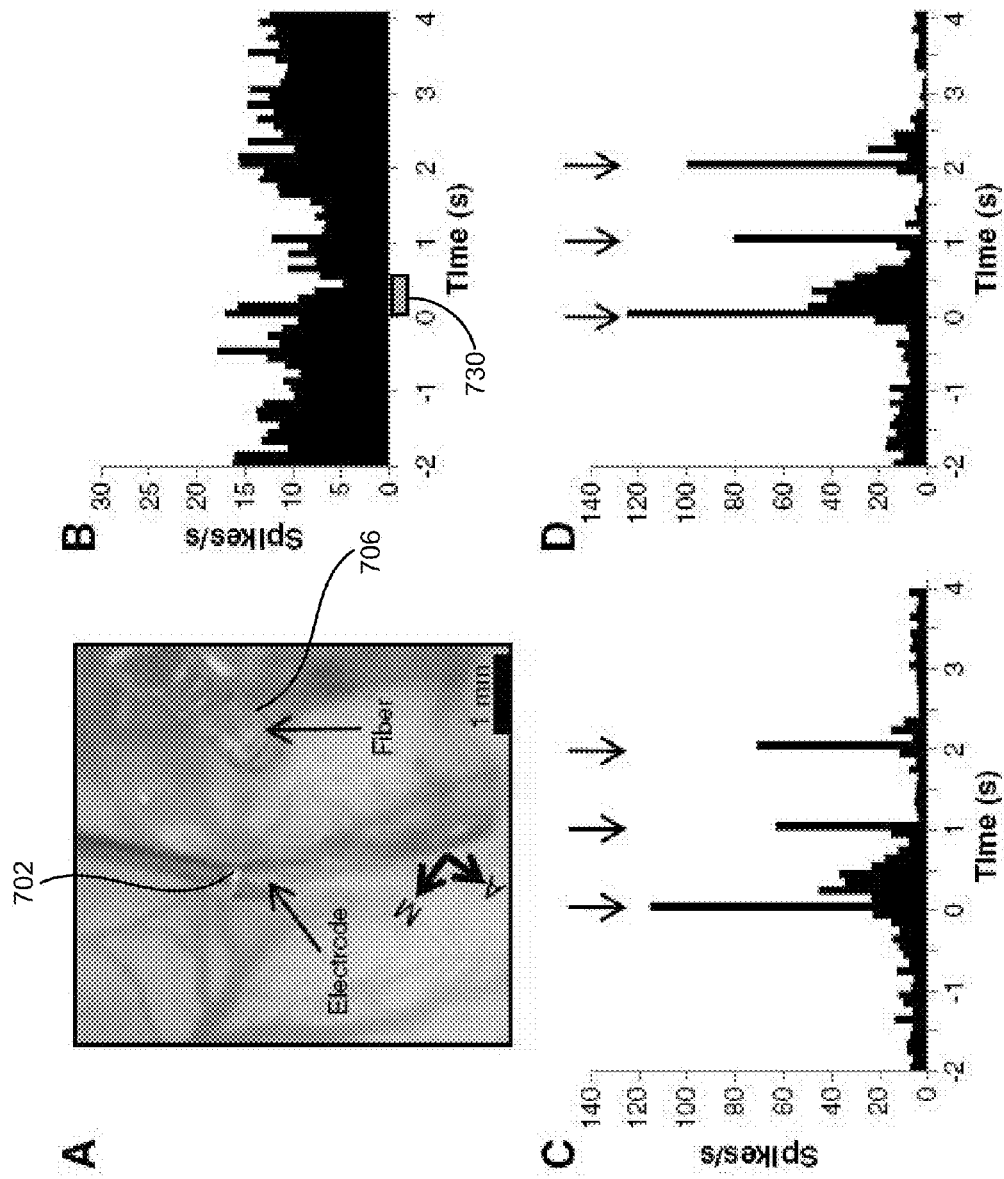
FIG. 7 illustrates that INS induces an inhibitory neural response and does not alter neuronal response to tactile stimulation in accordance with certain embodiments of the present disclosure.

Inhibitory Effect of INS Stimulation (Without Tactile Stimulation) in Somatosensory Cortex In addition to optical imaging, electrophysiological techniques are used to study the effects of INS on neuronal activity. FIG. 7 illustrates that INS induces an inhibitory neural response and does not alter neuronal response to tactile stimulation. FIG. 7A shows image of somatosensory cortex corresponding to barrel field showing electrode and fiber placement. Fiber stimulation site to electrode distance is approximately 1 mm. Electrode tip is placed 50 μm into cortex. FIG. 7B is PSTH showing modulation of neural response to INS (30 trials). The laser-induced inhibition of neural activity has a duration of approximately 1.5 s and is followed by a rebound. FIG. 7C shows PSTH of vibrotactile stimulation generated by a piezoelectric bender deflecting contralateral whiskers once at each arrow. Laser and whisker stimulation are interleaved. FIG. 7D shows PSTH of vibrotactile stimulation after INS. FIGS. 7C and D demonstrate that INS do not cause a loss of cortex functionally responding to sensory stimulation. Laser parameters are: $\lambda=1.875$ μm, repetition rate=100 Hz, pulse train duration=500 ms, pulse width=250 μs, radiant exposure=0.019 J/cm2, spot size=1200 μm. Hatched bar 730 in FIG. 7B represents the timing of the stimulus. "A" in the drawing indicates anterior; "M" indicates medial.

FIG. 7A displays the positioning of the electrode 702 and fiber 706, approximately 1 mm apart. This arrangement is similar for each experiment involving electrophysiological measurements. Units that are responsive to tactile stimulation are isolated to assess cortical function during INS. FIG. 7B displays the results of laser stimulation on spontaneous neural activity. Illustrated is a peristimulus time histogram (PSTH) resulting from the irradiation of somatosensory cortex (186 trials with intertrial intervals of 15 s; radiant exposure of 0.019 J/cm2, pulse width of 250 μs, pulse train length of 500 ms). Stimulus onset occurred at time zero and lasted for 500 ms (hashed bar on PSTH). It is observed that INS can lead to a reduction in firing rate that lasted approximately 1.5-2.0 s, followed by a return to baseline levels. This reduction in firing rate was statistically significant, as evaluated by comparing the two seconds prior to stimulation and the two seconds post stimulation onset (paired t-test, $\alpha=0.05$, −2000 ms to 0 ms: p<0.0046 0.0188, 2000 ms to 4000 ms p<9.55e−50). No statistical difference was observed between the two seconds before stimulation and the time region corresponding to 2-4 s after stimulation offset.

Cortex Remains Responsive During INS

The physiologic health of the cortex can be assessed through electrophysiological recordings of neuronal responses to tactile stimulation. In FIGS. 7C and D, tactile stimulation is delivered by a piezoelectric stimulator that deflected contralateral whiskers once at each arrow in the PSTH. During runs in which INS is interleaved with tactile stimulation, consistent, normal neural responses to tactile stimulation were recorded (FIG. 7C). The PSTH in FIG. 7D represents tactile stimulation alone after INS had been applied demonstrating no loss in functionality. These recordings from tactile stimulation demonstrate that the normal excitatory and inhibitory periods of post-stimulation responses are present. Thus, even after repeated presentation of INS for a period of over 2 h, normal neuronal tactile responses can remain intact indicating that INS does not cause damage to cortex which compromises neuronal activity.

Stability of INS Induced Responses

Stability of INS induced responses is important to consider when assessing the stimulation modality's efficacy for neuroscience applications and eventual translation to clinical studies. To examine the stability of INS induced responses, a sequence of PSTHs are produced by dividing the total number of INS trials into sequential 40 trial epochs.

Figure 8:
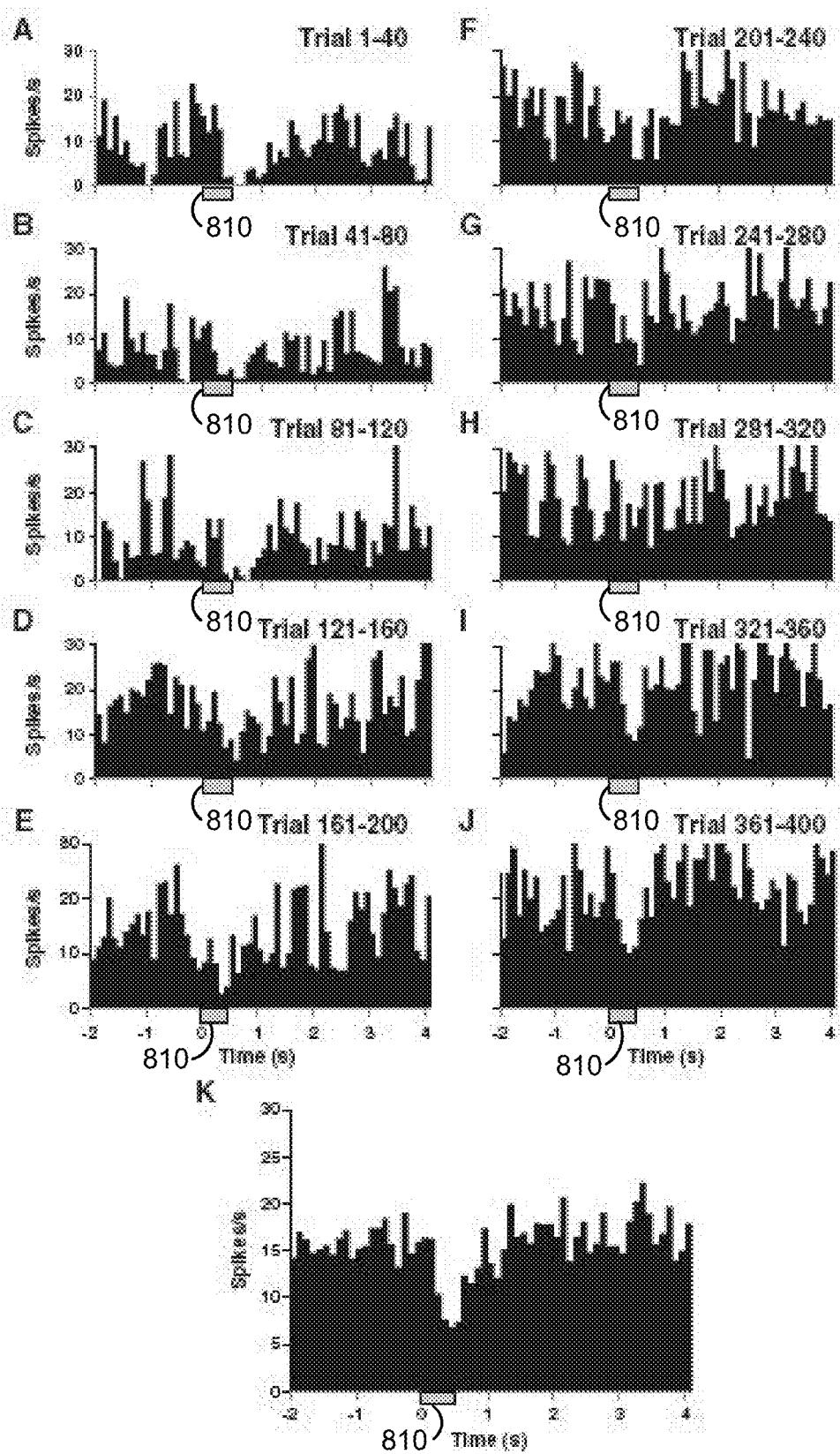
FIG. 8. shows that inhibitory effects of INS on neural activity are consistent over many trials in accordance with certain embodiments of the present disclosure.

FIG. 8 shows that inhibitory effect of INS on neural activity is consistent over many trials. FIG. 8A-J show PSTH mosaic of ten segments (40 trials per segment). The laser induced inhibition is strongest in the first 120 trials, then weakens but is evident through trials 361-400. FIG. 8K shows PSTH summation of all segments of FIG. 8A-J. Laser parameters are: $\lambda=1.875$ μm, repetition rate=200 Hz, pulse train duration=500 ms, pulse width=250 µs, radiant exposure=0.0549 J/cm2, spot size=850 µm. Hatch bars 810 represent the timing of the stimulus.

FIG. 8 displays a sequence of PSTHs recorded from a single unit in response to INS (radiant exposure 0.055 J/cm$^2$, spot size 850 µm, repetition rate of 200 Hz, pulse width 250 µs, train length 500 ms, 15 s intertrial interval). In most of the histograms, inhibition is most evident during the period from stimulus onset (time=0 s) to approximately 1 s. In this example, it can be seen that INS induced inhibition is readily apparent from trial 1 to at least trial 120, and although appears to weaken slightly subsequently, the signal is still evident as late as trials 360-400. Paired t-tests between the two seconds following stimulus onset and prestimulus periods indicate that the difference in spike rate is statistically significant ($\alpha$=0.05) for the summation of all trials (FIG. 8K) indicating that INS in rat somatosensory cortex has an immediate inhibitory effect on neuronal response, one which appears to remain present over many trials.

Figure 9:
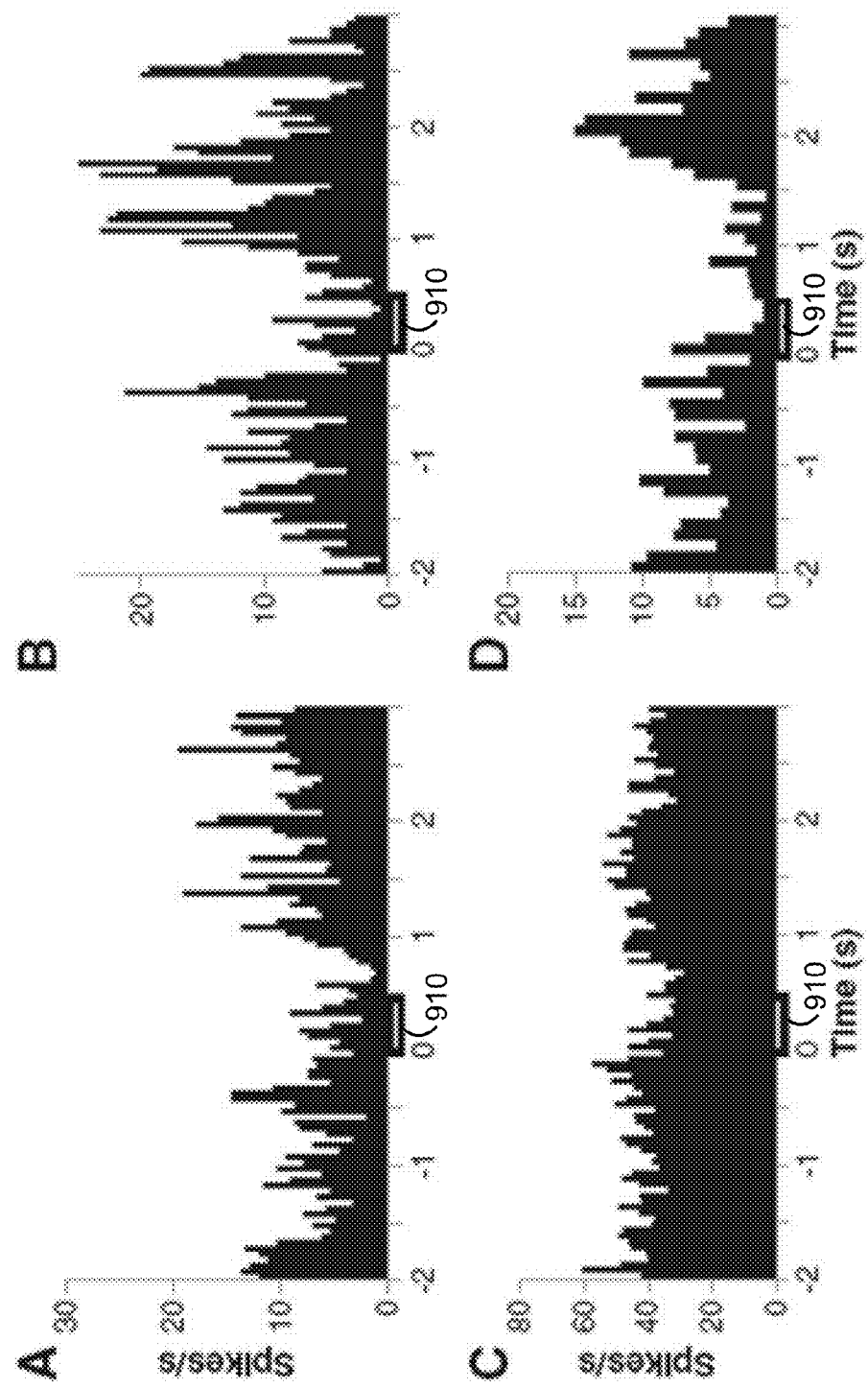
FIG. 9 shows repeatability of the neural INS inhibitory effects in accordance with certain embodiments of the present disclosure.

A separate experiment can be conducted to assess the stability of this effect at two separate time points during an experiment. FIG. 9 shows repeatability of the neural INS inhibitory effect. FIG. 9A shows PSTH of single unit in response to INS. FIG. 9B shows a second PSTH from the same unit taken approximately 30 min later. Laser parameters are: $\lambda$=1.875 µm, repetition rate=200 Hz, pulse train duration=500 ms, pulse width=250 µs, radiant exposure=0.078 J/cm$^2$, spot size=850 µm. FIGS. 9C-D show PSTHs from other experiments showing inhibition from different cells. Laser parameters are: $\lambda$=1.875 µm, repetition rate=100 Hz, pulse train duration=500 ms, pulse width=250 µs, radiant exposures: 0.043 J/cm$^2$ and 0.12 J/cm$^2$, spot sizes=880 µm and 840 µm. Inhibition can be observed regardless of baseline activity of a single unit. Hatch bars 910 in represent the timing of the stimulus.

FIG. 9A represents an initial PSTH taken over 30 trials separated by ITIs of 30 s. Again a period of statistically significant (paired t-test, −1 s to 0 s: p<0.01, 1 s to 2 s p<4.08E−5) inhibition of baseline activity was observed within the first 1 s after INS onset (spot size 850 µm, pulse train length 500 ms, pulse width 250 µs, radiant exposure of approximately 0.078 J/cm$^2$). The laser is then turned off and the cortex is allowed to rest for 30 min after which the experiment is repeated. FIG. 9B illustrates the PSTH recorded from single unit activity at the same location using the same laser parameters used to generate FIG. 9A. Again, a period of inhibition can be obtained within the first 1 s following INS (paired t-test, −1 s to 0 ms: p<0.03, 1 s to 2 s p<0.00038). This further demonstrates the repeatability of the inhibitory effect.

FIGS. 9C and D illustrate two separate single units from experiments performed on individual animals where INS generated an inhibitory response in each PSTH. The repetition rate can be set at either 100 and 200 Hz for each PSTH and the radiant exposures were 0.078 J/cm$^2$ and 0.019 J/cm$^2$ respectively, using a 500 ms pulse train and a pulse width of 250 µs. INS induced inhibition was significant (paired t-tests: FIG. 9C, 0 to 1 s vs. −1 to 0 s: p<0.0037, or vs. 1 to 2 s; p<0.000185; FIG. 9D 0 to 2 s vs. −2 to 0 s: p<0.0188, or 2 to 4 s p<0.0047). In total, statistically significant inhibitory responses were observed in all five animals studied in this fashion; excitatory responses were not observed. Thus, the effect of direct INS stimulation in rat somatosensory cortex appears to be inhibitory, as this effect was seen across all animals, different stimulation parameters, within different epochs of repeated INS stimulation, and during different recording periods within an experiment.

SUMMARY

It has been demonstrated that in brain slices CNS neurons can be excited using pulsed infrared light [Cayce et al., 2010]. Almost all previously published studies on INS of neural tissue have focused on the PNS [Duke et al., 2009; Fried et al., 2008]; Izzo et al., 2008; Jenkins et al., 2010; Rajguru et al., 2010]; Richter et al., 2010; Wells et al., 2007b; Wininger et al., 2009]. The present disclosure innovatively examine the effects of INS on cortical tissue in vivo. Using intrinsic signal imaging, it is found that INS induced changes in optical reflectance can show similarities to intrinsic signal responses previously reported for sensory stimuli presented to somatosensory or visual cortex [Chen et al., 2007; Grinvald, 1985; Roe, 2007; Ts'o et al., 1990; Tsytsarev et al., 2010; Vanzetta et al., 2005]. As assessed by optical imaging, the spatial extent of the INS stimulus can reveal a roughly 2 mm region of effect, demonstrating a localized response to INS in cortical tissue that is similar to the high spatial precision that has been well characterized in PNS applications [Duke et al., 2009; Fried et al., 2008; Izzo et al., 2008; Teudt et al., 2007; Wells et al., 2007b]. The amplitude of the intrinsic response can increase with increasing infrared light energy, produced either by increasing the stimulation frequency or by increasing the radiant energy of the laser (FIGS. 4 and 5). Changing the radiant exposure induced a linear response in peak signal magnitude compared to an exponential response demonstrated by changing the repetition rate. An exponential relationship was also observed in thalamocortical slices where stimulation threshold decreased with increasing repetition rate [Cayce et al., 2010]. That INS repetition rate can affect cortical activity differently than radiant exposures suggests total radiant exposure alone cannot fully explain the functional results. Infrared irradiation of the cortex did not appear to harm tissue, as both optical and neuronal signals were maintained, as shown with interleaved INS and tactile stimulation trials and normal subsequent measurements of tactile activation following 2-hour periods of repeated INS stimulation. Interestingly, cortical neuronal activity can be significantly inhibited during the 1 s period post INS onset. This inhibition was consistently observed across animals, different laser stimulation parameters, and sustained epochs of neuronal recording. This is the first report of INS evoking neuronal inhibition [Cayce et al., 2010; Fried et al., 2008; Izzo et al., 2006; Richter et al., 2010]; Teudt et al., 2007; Wells et al., 2007b].

Certain aspects of the present disclosure indicate a long sustained response similar to that seen in sensory-induced intrinsic signals, suggestive of a neuronal related response. Additionally, studies that have used electrical stimulation to stimulate either the whisker pad or the fore/hindpaw demonstrated similar time courses. Jones et al. demonstrated that a 1 s electrical stimulus (15 Hz, 1.6 mA) of the whisker pad produced a time course with a 6 second duration [Jones et al., 2001], and Bouchard et al. demonstrated that the time course of the reduced oxy-hemoglobin signal does not return to baseline until ~5 s post stimulation when electrical stimulation (3 Hz, 1 mA, for 4 s stimulation) is applied to the hindpaw [Bouchard et al., 2009]. A neural response is supported by the electrophysiology results which demonstrate clear, consistent inhibitory neuronal response, lasting approximately 1 s after laser stimulation onset (FIGS. 7-9). INS, like sensory induced changes, can lead to changes in reflectance through such factors as changes in blood volume, blood oxygenation, and light scattering. The 632 nm illuminant used targets the hemodynamic component and has been shown to correlate strongly with neuronal response.

The physiologic and anatomical differences between the PNS and the CNS can be used to help identify possible sources for the observed inhibitory response. In the PNS, all structures stimulated by infrared light have involved a nerve where stimulation could be applied and monitored downstream from the stimulation site. Conversely, the cerebral cortex of the brain consists of a neural network and contains inhibitory interneurons, and glial cells, astrocytes, ogliodendrocytes, and microglia, in a greater concentration than excitatory neurons.

Direct stimulation of cortex with light could evoke responses in excitatory neurons that would then propagate in numerous directions making it difficult to detect evoked excitatory responses or INS could evoke direct responses in the smaller inhibitory neurons or glial cells. A confounding issue is the depth at which the infrared light penetrates into the tissue. In certain embodiments, the wavelength of light (1.875 µm) penetrates approximately 300-600 µm into tissue, where intensity decays exponentially following Beer's law [Cayce et al., 2010; Hale and Querry, 1973]. This indicates that mainly layers I and II of cortex are stimulated with only a small percentage of photons reaching layer III. A higher number of inhibitory neurons and astrocytes are present in layers I and II than excitatory neurons which are mainly located in layers III/IV [Helmstaedter et al., 2008; Takata and Hirase, 2008]. However, the dendritic tree of the pyramidal cells located in deeper layers project up to the superficial layers of cortex and will contribute to the absorption of infrared energy. Astrocytes present another possible component underlying the INS-induced response. It has been suggested that astrocytes have a role in generating hemodynamic responses (Hillman, 2007; Schummers et al., 2008; Takano et al., 2006; Wang et al., 2006). It can be demonstrated that astrocytes have an active role in modulating neuronal transmission (Bowser and Khakh, 2004; Cunha, 2008; Koizumi et al., 2003; Kozlov et al., 2006; Perea et al., 2009).

Correlation of Intrinsic Optical Signal and Neuronal Inhibition

INS can cause inhibition whereas all other INS studies evoked excitation [Cayce et al., 2010; Fried et al., 2008; Izzo et al., 2006; Teudt et al., 2007; Wells et al., 2007b]. Electrodes can be those typically used for extracellular recordings and isolate excitatory neuronal activity quite readily (e.g. FIGS. 7C and D). Neurons can be sampled from the superficial cortical layers; some recordings can be also taken from deeper layers. The INS related neural activity is not limited to a specific depth or region of somatosensory cortex. In certain embodiments, it is more likely to sample cells with detectable spontaneous activity or clear tactilely driven response. In certain embodiments, tungsten microelectrodes can likely bias towards sampling large pyramidal neurons and not responses from smaller inhibitory neurons. While it is possible that INS had a suppressive effect on apical pyramidal cell dendrites in the superficial layers, it is also possible that INS has an excitatory effect on inhibitory neurons in superficial layers, resulting in the suppressed pyramidal neuronal responses. Feng et al. recently demonstrated that infrared light can increase the GABA current in isolated single cell recordings using cultured rat neurons [Feng et al., 2010], raising the possibility that some of the effects we observed may be direct effects on inhibitory neurons. Given the robust optical signals obtained with INS and the fact that our electrodes are biased towards larger neurons, it is likely that the predominant INS effect is preferential activation of inhibitory neurons. This is consistent with the effective penetration depth of the INS wavelength and stimulation parameters used here, which is likely to reach primarily layers I-II where inhibitory neurons are a predominant cellular component. Similar experiments can be conducted in other cortical areas and other. Although many studies of cortical function emphasize the correlation of intrinsic signal magnitude with excitatory (presumably pyramidal) neuronal response, this is clearly not always the case. Subthreshold neuronal responses also have been highlighted as significant components of intrinsic cortical signals [Das and Gilbert, 1995; Grinvald et al., 1994; Toth et al., 1996]. However, association of intrinsic optical signals with inhibitory neuron activation is less well documented.

Certain aspects of the present disclosure are directed to the size of the laser stimulation fiber. In certain embodiments, a 400 µm diameter fiber is positioned at distances up to 1.1 mm from the cortex, resulting in a spot size of up to 800 µm. The large size of the activation spot can have the effect of recruiting additional inhibitory circuits in somatosensory cortex. There are many examples of inhibitory effect of nearby barrels on the whisker barrel of interest [Derdikman et al., 2003; Simons and Carvell, 1989]. In visual cortex, larger size stimulation very frequently leads to inhibition [Ghose, 2009; Levitt and Lund, 1997]. This is due to additional inhibitory circuits that are activated when the spot size goes beyond the receptive field size. This is a common feature of cortical circuitry and could underlie the basis for the observed inhibitory responses. Whether excitatory/inhibitory effect is related to laser spot size would best be addressed in INS experiments using fibers of different diameters.

Example 2

Surgical Procedure

In short, male Long Evan rats (300-500 g) can be anesthetized using 50% urethane solution (1.33 g/kg). The toe-pinch test can be used to ensure the animal was in a deep state of anesthesia. A tracheotomy can be performed to allow for ventilation of the animal during the experiment. Once the tracheotomy is completed the animal was placed in a stereotactic frame for the craniotomy procedure. A midline incision can be made along the cranium of the animal and soft tissue was blunt dissected away from the underlying bone. The margins of the craniotomy to expose somatosensory cortex can be 2 mm rostral, 5 mm caudal, and 7 mm lateral with respect to bregma. A dental burr can be used to remove the bone overlaying somatosensory cortex. Once the craniotomy was completed, a durotomy can be performed to remove the dura overlaying the cortex. Mannitol (20% concentration) can be given IP to control brain swelling. Warm 3% agar can be used to stabilize the cortex and a glass coverslip can be placed on the agar to create an imaging window for optical imaging. A small portion of agar can be dissected away to create an access port for placement of the optical fiber for application of INS.

Infrared Neural Stimulation Parameters

A 400 µm fiber can be placed ~50-1000 µm away from cortex in access port created in the agar. In certain embodiments, wavelengths tested for these experiments can be for example 1.875 µm and 1.94 µm. The following parameters can be used to directly stimulate somatosensory cortex corresponding to the contralateral whiskers and/or forepaw. Repetition rate can be varied between 10-200 Hz. Pulse width was held constant at about 250 µm. Radiant energy can have a range between about 0.01-0.5 $J/cm^2$ which can be dependent on the stimulation parameters used in a given experiment. Stimulation trains of 500 ms can be delivered to the cortex spaced 15-30 seconds apart and interleaved with other stimulation conditions described in the optical imaging methods.

Optical Imaging

Intrinsic optical imaging can be used to visualize the hemodynamic response related to INS of somatosensory cortex. A CCD camera (e.g. RED SHIRT) and imaging software can be used to collect images of the cortex under 632 nm light at about 5 frames per second. Images can be acquired for about 8-16 seconds for each stimulation condition to constitute one imaging trial, and 20 to 50 imaging trials can be collected to comprise one imaging run. A single imaging trial contained at least a blank condition and one stimulation condition. Stimulation conditions can include laser stimulation using parameters previously outlined, mechanical stimuli delivered via a piezoelectric, or a combination of the two delivered simultaneously. Piezo electric stimulation can be delivered to the forepaw digit or whisker using 8 Hz pulse train to induce hemodynamic response that is measurable using intrinsic optical imaging. Mechanical stimulus of the animal can serve as a control to ensure cortex functionality and to help demonstrate lack of damage resulting from the laser.

Single Unit Electrophysiology

Single unit electrophysiology can be used to establish neural origin related to optical signals induced by INS. Tungsten microelectrodes (1-3 MΩ) can be inserted into cortex 50-500 μm corresponding to the forepaw or whisker as identified through piezoelectric stimulation. The optical fiber can be placed approximately 1 mm away from the electrode to ensure no thermal artifact was observed. Signals can be filtered and digitized using a 16 channel AM-Systems differential amplifier using 300-5K bandpass filter. Peristimulus time histograms (PSTH) can be generated using DATAVIEW software. T-test analysis can be used to determine statistical significance in changes observed in the PSTH related to laser stimulation.

Results

Figure 10:
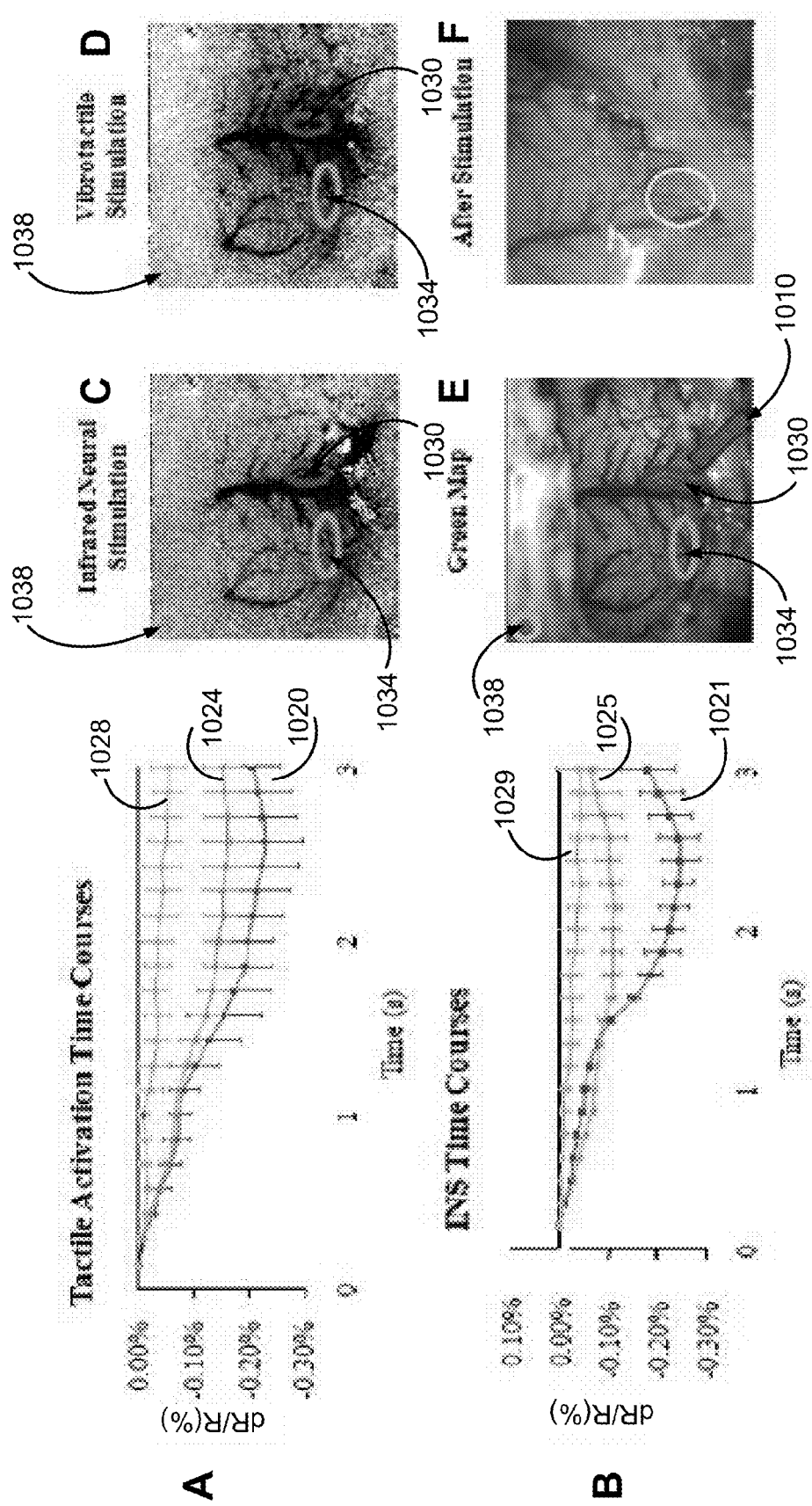
FIG. 10 shows that INS produces a similar change in diffuse reflected light similar to the signal generated by mechanical stimulation of the animal's forepaw or whisker in accordance with certain embodiments of the present disclosure.

FIG. 10 shows that Infrared neural stimulation produces a similar change in diffuse reflected light similar to the signal generated by mechanical stimulation of the animal's forepaw or whisker. FIG. 10 shows that intrinsic optical imaging demonstrates that INS induces similar responses to that of mechanical stimulation of the fore paw. FIG. 10A shows time course of optical signal related to tactile stimulation. FIG. 10B shows timecourse of optical signal related to INS. FIGS. 10C and D show subtraction maps for INS of cortex and tactile stimulation of forepaw with mask locations identify in regions of interest. FIG. 10E shows a blood vessel map taken under green light to identify blood vessel map. Box 1010 identifies fiber location. FIG. 10F shows that a image of cortex through surgical microscope demonstrates no visible signs of damage to cortex from INS. The mask 1030 corresponds to a forepaw ROI. The mask 1034 corresponds to a projection ROI. The mask 1038 corresponds to a control ROI (bone). Timecourses 1020, 1021 corresponds to the mask 1030. Timecourses 1024, 1025 corresponds to the mask 1034. Timecourses 1028, 1029 correspond to the mask 1038.

The subtraction image and timecourse related to tactile stimulation (FIGS. 10 A&D) can be generated by stimulating digit 3 of the contralateral forepaw using an 8 Hz, 3 second vibrotactile stimulus delivered with a piezoelectric stimulator. Infrared neural stimulation generated the timecourse and subtraction map seen in FIG. 10 B&C using a 200 Hz stimulus for 500 ms at a wavelength of 1.94 μm and 250 μJ/cm$^2$ of energy through a 400 μm fiber. The timecourse 1020 for both INS and tactile stimulation correspond to the region of somatosensory cortex activated directly by tactile stimulation. The optical fiber 1010 can be oriented to stimulate this area of cortex to allow for direct comparison between each stimulation condition. The mask 1034 corresponds to a projection area near motor cortex which suggests activation in the forepaw ROI projects to the cortex under the mask 1034. No damage was observed after several hours of imaging while stimulation the cortex with the laser (FIG. 10F).

Figure 11:
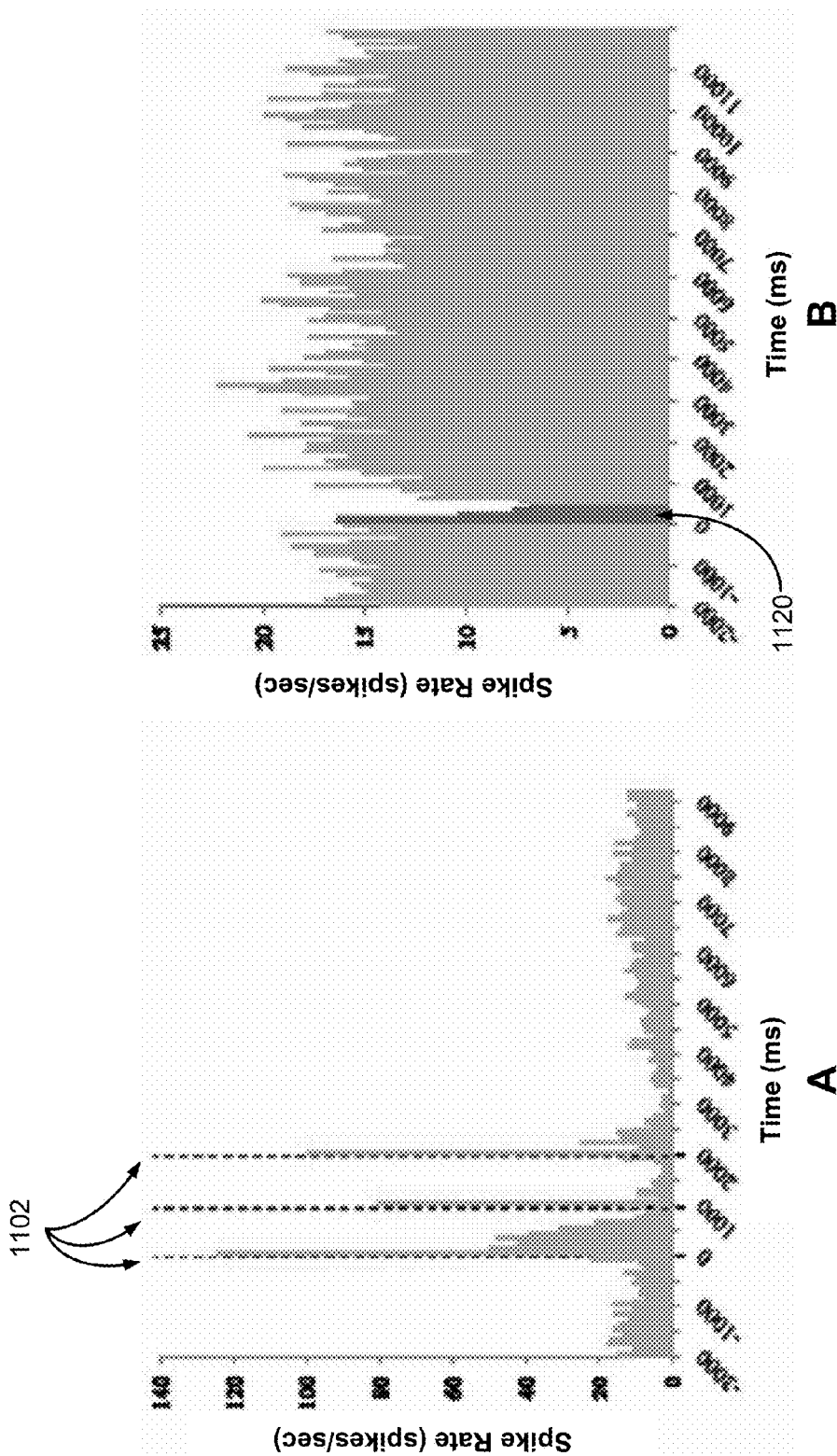
FIG. 11 shows that a 1 Hz, 3 sec train of piezoelectric pulses can be delivered to the contralateral whisker field to generate the PSTH in accordance with certain embodiments of the present disclosure.

Single unit recordings can be collected for both INS and tactile stimulation of the barrel fields related to the contralateral whiskers. FIG. 11 shows that a 1 Hz, 3 sec train of piezoelectric pulses can be delivered to the contralateral whisker field to generate the PSTH.

FIG. 11 illustrates that electrophysiological analysis of INS shows inhibitory response in contrast to excitatory response associated with mechanical stimulation. FIG. 11A shows PSTH generated by 3 second train of 1 Hz piezoelectric stimulation of contralateral whiskers. Dashed lines 1102 indicate piezoelectric pulse. FIG. 11B shows PSTH of inhibitory response related to INS. Area 1120 indicates stimulus onset. INS parameters are: λ=1.875 μm, 500 ms pulse train length, 0.019 J/cm$^2$, 250 μs pulse width. Each dashed line 1102 represents the location in time of each pulse delivered by the piezoelectric stimulator. In all cases, mechanical stimulation of the animal can produce an excitatory response from neurons located in somatosensory cortex. Infrared neural stimulation of this same location demonstrates that INS has an overall inhibitory response on neuronal firing. A 500 ms train of 100 Hz pulses with a pulse width of 250 μs can be delivered to a cortex using a wavelength of light at 1.875 μm. The pulse energy can be measured to be 0.019 J/cm$^2$ and was delivered via a 400 μm optical fiber. The observed inhibition lasts for approximately 1 second after start of stimulus delivery.

This example demonstrates the INS can be used to inhibit neuronal activation in vivo. Infrared neural stimulation generates intrinsic optical signals with similar timecourses to signals generated by mechanical stimulation of an animal.

The PSTH contained in FIG. 11B demonstrates that INS inhibits neuronal activity for approximately 1 second after onset of stimulation. In contrast, all prior studies which have employed INS as a stimulation modality, mainly in the PNS, have demonstrated excitatory responses that are frequency locked with the laser [B17-20].

The differences in neural activation between the CNS and PNS can be explained by the anatomy and physiology of the tissue. In the PNS, the target tissue is mainly axons organized in nerve bundles as parallel tracts. The majority of the ion channels are sodium and potassium channels which are used to propagate action potentials down an axon to the next synapse. Additionally, the ion channels in myelinated axons are located at the Nodes of Ranvier further isolating the excitatory ion channels. Therefore, stimulation of the axons only leads to excitation downstream. The somatosensory cortex is organized into six distinct cortical layers. Layers V and VI mainly contain axons and some cell bodies which carries information to and from the neurons located in layers IV and III. Layers I and II mainly contain the dendrytic tree from neurons contained in the deeper layers and also contain a large concentration of astrocytes and other support cells [B21]. Additionally, layers I, II, and III contain inhibitory interneurons. In certain embodiments, the wavelengths of light used only have a penetration depth between 100-400 μm indicating that the superficial layers (I,II,III) absorb the majority of the infrared energy. This organization of somatosensory cortex combined with the penetration depth of the light used to perform INS can be a possible explanation for the observed inhibitory response from laser stimulation.

The foregoing description of the exemplary embodiments of the invention has been presented only for the purposes of illustration and description and is not intended to be exhaustive or to limit the present disclosure to the precise forms disclosed. Many modifications and variations are possible in light of the above teaching.

The embodiments were chosen and described in order to explain the principles of the present disclosure and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present disclosure is defined by the appended claims rather than the foregoing description and the exemplary embodiments described therein.

REFERENCE LIST A

[A1] Agmon, A., Connors, B. W., 1991. Thalamocortical responses of mouse somatosensory (barrel) cortex in vitro. Neuroscience 41, 365-379.

[A2] Blanton, M. G., Lo Turco, J. J., Kriegstein, A. R., 1989. Whole cell recording from neurons in slices of reptilian and mammalian cerebral cortex. J. Neurosci. Methods 30, 203-210.

[A3] Bouchard, M. B., Chen, B. R., Burgess, S. A., Hillman, E. M. C., 2009. Ultra-fast multispectral optical imaging of cortical oxygenation, blood flow, and intracellular calcium dynamics. Opt. Express 17, 15670-15678.

[A4] Bowser, D. N., Khakh, B. S., 2004. ATP excites interneurons and astrocytes to increase synaptic inhibition in neuronal networks. J. Neurosci. 24, 8606-8620.

[A5] Cayce, J. M., Kao, C. C., Malphrus, J. D., Konrad, P. E., Mahadevan-Jansen, A., Jansen, E. D., 2010. Infrared neural stimulation of thalamocortical brain slices. STQE. IEEE J. 16, 565-572.

[A6] Chapin, J. K., Lin, C. S., 1984. Mapping the body representation in the SI cortex of anesthetized and awake rats. J. Comp. Neurol. 229, 199-213.

[A7] Chen, L. M., Turner, G. H., Friedman, R. M., Zhang, N., Gore, J. C., Roe, A. W., Avison, M. J., 2007. High-resolution maps of real and illusory tactile activation in primary somatosensory cortex in individual monkeys with functional magnetic resonance imaging and optical imaging. J. Neurosci. 27, 9181-9191.

[A8] Cunha, R. A., 2008. Different cellular sources and different roles of adenosine: A1 receptor-mediated inhibition through astrocytic-driven volume transmission and synapse-restricted A2A receptor-mediated facilitation of plasticity. Neurochem. Int. 52, 65-72.

[A9] Das, A., Gilbert, C. D., 1995. Long-range horizontal connections and their role in cortical reorganization revealed by optical recording of cat primary visual cortex. Nature 375, 780-784.

[A10] Derdikman, D., Hildesheim, R., Ahissar, E., Arieli, A., Grinvald, A., 2003. Imaging spatiotemporal dynamics of surround inhibition in the barrels somatosensory cortex. J. Neurosci. 23, 3100-3105.

[A11] Duke, A. R., Cayce, J. M., Malphrus, J. D., Konrad, P., Mahadevan-Jansen, A., Jansen, E. D., 2009. Combined optical and electrical stimulation of neural tissue in vivo. J. Biomed. Opt. 14, 060501-060503.

[A12] Dunn, A. K., Devor, A., Dale, A. M., Boas, D. A., 2005. Spatial extent of oxygen metabolism and hemodynamic changes during functional activation of the rat somatosensory cortex. Neuroimage 27, 279-290.

[A13] Feng, H.-J., Kao, C., Gallagher, M. J., Jansen, E. D., Mahadevan-Jansen, A., Konrad, P. E., Macdonald, R. L., 2010. Alteration of GABAergic neurotransmission by pulsed infrared laser stimulation. J. Neurosci. Methods 192, 110-114.

[A14] Fried, N. M., Lagoda, G. A., Scott, N. J., Su, L.-M., Burnett, A. L., 2008. Noncontact stimulation of the cavernous nerves in the rat prostate using a tunable-wavelength thulium fiber laser. J. Endourol. 22, 409-414.

[A15] Fritsch, G., Hitzig, E., 1870. Ueber die elektrische Erregbarkeit der Grosshirns. Arch. Anat. Physiol. Wiss. Med. 37, 300-332.

[A16] Galvani, 1791. Bon. Sci. Art. Inst. Acad. Comm. 363-418.

[A17] Ghose, G. M., 2009. Attentional modulation of visual responses by flexible input gain. J. Neurophysiol. 101, 2089-2106.

[A18] Grinvald, A., 1985. Real-time optical mapping of neuronal activity: from single growth cones to the intact mammalian brain. Annu Rev. Neurosci. 8, 263-305.

[A19] Grinvald, A., Lieke, E. E., Frostig, R. D., Hildesheim, R., 1994. Cortical point-spread function and long-range lateral interactions revealed by real-time optical imaging of macaque monkey primary visual cortex. J. Neurosci. 14, 2545-2568.

[A20] Hale, G. M., Querry, M. R., 1973. Optical constants of water in the 200-nm to 200-μm wavelength region. Appl. Opt. 12, 555-563.

[A21] Helmstaedter, M., Staiger, J. F., Sakmann, B., Feldmeyer, D., 2008. Efficient recruitment of layer 2/3 interneurons by layer 4 input in single columns of rat somatosensory cortex. J. Neurosci. 28, 8273-8284.

[A22] Hillman, E. M. C., 2007. Optical brain imaging in vivo: techniques and applications from animal to man. J. Biomed. Opt. 12, 051402-051428.

[A23] Izzo, A. D., Richter, C.-P., Jansen, E. D., Joseph, T., Walsh, J., 2006. Laser stimulation of the auditory nerve. Lasers Surg. Med. 38, 745-753.

[A24] Izzo, A. D., Walsh, J. T., Ralph, H., Webb, J., Bendett, M., Wells, J., Richter, C.-P., 2008. Laser stimulation of auditory neurons: effect of shorter pulse duration and penetration depth. Biophys. J. Biophys. 107, 117150.

[A25] Jenkins, M. W., Duke, A. R., Gu S, Doughman Y, Chiel, H. J., Fujioka H, Watanabe M, Jansen, E. D., Rollins, A. M., 2010. Optical pacing of the embryonic heart. Nat. Photon. 4, 623-626.

[A26] Jones, M., Berwick, J., Johnston, D., Mayhew, J., 2001. Concurrent optical imaging spectroscopy and laser-Doppler flowmetry: the relationship between blood flow, oxygenation, and volume in rodent barrel cortex. Neuroimage 13, 1002-1015.

[A27] Kao, C. Q., Coulter, D. A., 1997. Physiology and pharmacology of corticothalamic stimulation-evoked responses in rat somatosensory thalamic neurons in vitro. J. Neurophysiol. 77, 2661-2676.

[A28] Koizumi, S., Fujishita, K., Tsuda, M., Shigemoto-Mogami, Y., Inoue, K., 2003. Dynamic inhibition of excitatory synaptic transmission by astrocyte-derived ATP in hippocampal cultures. Proc. Natl. Acad. Sci. USA 100, 11023-11028.

[A29] Kozlov, A. S., Angulo, M. C., Audinat, E., Charpak, S., 2006. Target cell-specific modulation of neuronal activity by astrocytes. Proc. Natl. Acad. Sci. 103, 10058-10063.

[A30] Levitt, J. B., Lund, J. S., 1997. Contrast dependence of contextual effects in primate visual cortex. Nature 387, 73-76.

[A31] Paxinos, G., Watson, C., 2007. The Rat Brain in Stereotaxic Coordinates/George Paxinos, Charles Watson. Elsevier, Amsterdam.

[A32] Perea, G., Navarrete, M., Araque, A., 2009. Tripartite synapses: astrocytes process and control synaptic information. Trends Neurosci. 32, 421-431.

[A33] Petersen, C. C. H., 2007. The functional organization of the barrel cortex. Neuron 56, 339-355.

[A34] Rajguru, S. M., Matic, A. I., Robinson, A. M., Fishman, A. J., Moreno, L. E., Bradley, A., Vujanovic, I., Breen, J., Wells, J. D., Bendett, M., Richter, C.-P., 2010. Optical cochlear implants: Evaluation of surgical approach and laser parameters in cats. Hear. Res. 269, 102-111.

[A35] Richter, C. P., Matic, A. I., Wells, J. D., Jansen, E. D., Walsh, J. T., 2010. Neural stimulation with optical radiation. Laser Photon. Rev. 5, 68-80.

[A36] Roe, A. W., 2007. Long-term optical imaging of intrinsic signals in anesthetized and awake monkeys. Appl. Opt. 46, 1872-1880.

[A37] Roux, F. E., Tremoulet, M., 2002. Organization of language areas in bilingual patients: a cortical stimulation study. J. Neurosurg. 97, 857-864.

[A38] Schummers, J., Yu, H., Sur, M., 2008. Tuned responses of astrocytes and their influence on hemodynamic signals in the visual cortex. Science 320, 1638-1643.

[A39] Simons, D. J., Carvell, G. E., 1989. Thalamocortical response transformation in the rat vibrissa/barrel system. J. Neurophysiol. 61, 311-330.

[A40] Starr, P. A., Christine, C. W., Theodosopoulos, P. V., Lindsey, N., Byrd, D., Mosley, A., Marks Jr., W. J., 2002. Implantation of deep brain stimulators into the subthalamic nucleus: technical approach and magnetic resonance imaging-verified lead locations. J. Neurosurg. 97, 370-387.

[A41] Takano, T., Tian, G.-F., Peng, W., Lou, N., Libionka, W., Han, X., Nedergaard, M., 2006. Astrocyte-mediated control of cerebral blood flow. Nat. Neurosci. 9, 260-267. Takata, N., Hirase, H., 2008. Cortical layer 1 and layer 2/3 astrocytes exhibit distinct calcium dynamics in vivo. PLoS One 3, e2525.

[A42] Teudt, I. U., Nevel, A. E., Izzo, A. D., Walsh Jr., J. T., Richter, C. P., 2007. Optical stimulation of the facial nerve: a new monitoring technique? Laryngoscope 117, 1641-1647.

[A43] Toth, L. J., Rao, S. C., Kim, D. S., Somers, D., Sur, M., 1996. Subthreshold facilitation and suppression in primary visual cortex revealed by intrinsic signal imaging. Proc. Natl. Acad. Sci. USA 93, 9869-9874.

[A44] Ts'o, D. Y., Frostig, R. D., Lieke, E. E., Grinvald, A., 1990. Functional organization of primate visual cortex revealed by high resolution optical imaging. Science 249, 417-420.

[A45] Tsytsarev, V., Pope, D., Pumbo, E., Garver, W., 2010. Intrinsic optical imaging of directional selectivity in rat barrel cortex: application of a multidirectional magnetic whisker stimulator. J. Neurosci. Methods 189, 80-83.

[A46] van Gemert, M. J. C., Welch, A. J., 1995. Approximate solutions for heat conduction: time constants. In: Welch, A. J., van Gemert, M. J. C. (Eds.), Optical-Thermal Response of Laser-Irradiated Tissue. Plenum Press, New York.

[A47] Vanzetta, I., Hildesheim, R., Grinvald, A., 2005. Compartment-resolved imaging of activity-dependent dynamics of cortical blood volume and oximetry. J. Neurosci. 25, 2233-2244.

[A48] Wang, X., Lou, N., Xu, Q., Tian, G.-F., Peng, W. G., Han, X., Kang, J., Takano, T., Nedergaard, M., 2006. Astrocytic Ca2+ signaling evoked by sensory stimulation in vivo. Nat. Neurosci. 9, 816-823.

[A49] Wells, J., Kao, C., Jansen, E. D., Konrad, P., Mahadevan-Jansen, A., 2005a. Application of infrared light for in vivo neural stimulation. J. Biomed. Opt. 10, 064003.

[A50] Wells, J., Kao, C., Mariappan, K., Albea, J., Jansen, E. D., Konrad, P., Mahadevan-Jansen, A. 2005b. Optical stimulation of neural tissue in vivo. Opt. Lett. 30, 504-506.

[A51] Wells, J., Kao, C., Konrad, P., Milner, T., Kim, J., Mahadevan-Jansen, A., Jansen, E. D., 2007a. Biophysical mechanisms of transient optical stimulation of peripheral nerve. Biophys. J. 93, 2567-2580.

[A52] Wells, J., Konrad, P., Kao, C., Jansen, E. D., Mahadevan-Jansen, A., 2007b. Pulsed laser versus electrical energy for peripheral nerve stimulation. J. Neurosci. Methods 163, 326-337.

[A53] Wininger, F. A., Schei, J. L., Rector, D. M., 2009. Complete optical neurophysiology: toward optical stimulation and recording of neural tissue. Appl. Opt. 48, D218-D224.

REFERENCE LIST B

[B1] S. D. Schoonhoven, "Models and analysis of compound nerve action potentials," Crit. Rev. Biomed. Eng., v. 19, 47-111, 1991.

[B2] K. Cole, "Membranes, Ions, and Impulses: A Chapter of Classical Biophysics," Berkely: University of California Press, 1968, p. 569.

[B3] B. Hille, Ion Channels of Excitable Membranes, 3 ed. Sunderland, Mass.: Sinaure Associates, 2001.

[B4] C. Huang "Characterization of voltage-gated sodium channel blockers by electrical stimulation and fluorescence detection of membrane potential," Nat. Biotechnology, vol. 24, 439-446, 2006.

[B5] R. Plonsey and R. Barr, Bioelectricity: A Quantitative Approach, 2 ed.: Kluwer Academic, 2000.

[B6] E. Civillico and D. Contreras, "Comparison of Responses to Electrical Stimulation and Whisker Deflection Using Two Different Voltage-Sensitive Dyes in Mouse Barrel Cortex in Vivo," Journal of Membrane Biology, vol. 208, pp. 171-182, 2005.

[B7] K. McGill, et. al, "On the nature and elimination of stimulus artifact in nerve signals evoked and recorded using surface electrodes," IEEE Trans Biomed Eng, vol. 29, pp. 129-37, 1982.

[B8] J. Wells, C. Kao, K. Mariappan, J. Albea, E. D. Jansen, P. Konrad, and Mahadevan-Jansen, "Optical stimulation of neural tissue in vivo," Opt Lett, vol. 30, pp. 504-6, Mar. 1, 2005.

[B9] J. Wells, S. Thomsen, P. Whitaker, E. D. Jansen, C. C. Kao, P. E. Konrad, and A. Mahadevan-Jansen, "Optically mediated nerve stimulation: Identification of injury thresholds," Lasers Surg Med, vol. 39, pp. 513-26, July 2007.

[B10] J. Wells, C. Kao, P. Konrad, T. Milner, J. Kim, A. Mahadevan-Jansen, and E. D. Jansen, "Biophysical mechanisms of transient optical stimulation of peripheral nerve," Biophys J, vol. 93, pp. 2567-80, Oct. 1, 2007.

[B11] W. H. Wu, R. Ponnudurai, J. Katz, C. B. Pott, R. Chilcoat, A. Uncini, S. Rapoport, P. Wade, and A. Mauro, "Failure to confirm report of light-evoked response of peripheral nerve to low power helium-neon laser light stimulus," Brain Res, vol. 401, pp. 407-8, Jan. 20, 1987.

[B12] P. Balaban, R. Esenaliev, T. Kant, E. Kutomkina, V. Letokhov, A. Oraevsky, and N. Ovcharenko, "He—Ne laser irradiation of single identified neurons," Lasers Surg Med, vol. 12, pp. 329-37, 1992.

[B13] D. Bragard, A. C. Chen, and L. Plaghki, "Direct isolation of ultra-late (C-fibre) evoked brain potentials by CO2 laser stimulation of tiny cutaneous surface areas in man," Neurosci Lett, vol. 209, pp. 81-4, May 10, 1996.

[B14] D. Gigo-Benato, et al., "Low-power laser biostimulation enhances nerve repair after end-to-side neurorrhaphy: a double-blind randomized study in the rat median nerve model," Lasers in Medical Science, vol. 19, pp. 57-65, 2004.

[B15] S. Ilic, S. Leichliter, J. Streeter, A. Oron, L. DeTaboada, and U. Oron, "Effects of Power Densities, Continuous and Pulse Frequencies, and Number of Sessions of Low-Level Laser Therapy on Intact Rat Brain," Photomedicine and Laser Surgery, vol. 24, pp. 458-466, 2006.

[B16] E. S. Boyden, F. Zhang, E. Bamberg, G. Nagel, and K. Deisseroth, "Millisecond-timescale, genetically targeted optical control of neural activity," Nat Neurosci, vol. 8, pp. 1263-8, September 2005.

[B17] A. D. Izzo, J. T. Walsh, Jr., E. D. Jansen, M. Bendett, and C. P. Richter, "Optical parameter variability in laser nerve stimulation: a study of pulse duration, repetition rate, and wavelength," IEEE Trans Biomed Eng, vol. 54, pp. 1108-14, June 2007.

[B18] J. Wells, P. Konrad, C. Kao, E. D. Jansen, and A. Mahadevan-Jansen, "Pulsed laser versus electrical energy for peripheral nerve stimulation," J Neurosci Methods, vol. 163, pp. 326-37, Jul. 30, 2007.

[B19] N. M. Fried, G. A. Lagoda, N. J. Scott, L.-M. Su, and A. L. Burnett, "Noncontact Stimulation of the Cavernous Nerves in the Rat Prostate Using a Tunable-Wavelength Thulium Fiber Laser," Journal of Endourology, vol. 22, pp. 409-414, 2008.

[B20] I. U. Teudt, A. E. Nevel, A. D. Izzo, J. T. Walsh, Jr., C. P. Richter, "Optical stimulation of the facial nerve: a new monitoring technique?," Laryngoscope, vol. 117, pp. 1641-7, September 2007.

[B21] N. Takata and H. Hirase, "Cortical layer 1 and layer 2/3 astrocytes exhibit distinct calcium dynamics in vivo," PLoS One, vol. 3, p. e2525, 2008.

What is claimed is:

1. An apparatus for applying infrared neural stimulation (INS) to the central nervous system (CNS) of a target, the apparatus comprising:
a generator generating a pulsed infrared laser beam having a preset pulse train duration in a range of about 500 ms to about 1000 ms, wavelength, and radiant exposure; a control computer configured to execute a control software code, wherein the control software code, when executed, is configured to send a plurality of pulses to the generator to control the generator to generate the pulsed infrared laser beam;
an imaging system separate from the control computer, wherein the imaging system is configured to determine a stimulus condition or a blank condition of the target, and initiate the control software code at the control computer based on the stimulus or blank condition of the target; and
an optical medium having a numerical aperture and is adapted to be positioned at a predetermined distance from a stimulation site of the CNS to deliver the pulsed infrared laser beam at the stimulation site of the CNS, wherein the pulsed infrared laser beam is configured to penetrate a predetermined penetration depth of the stimulation site to evoke a response from the CNS, wherein the wavelength of the pulsed infrared laser beam is predetermined based on the penetration depth of the stimulation site of the CNS, and the radiant exposure of the pulsed infrared laser is predetermined based on the numerical aperture of the optical medium and the distance of the optical medium from the stimulation site.

2. The apparatus of claim 1, wherein the penetration depth is in a range of about 100 μm to about 400 μm.

3. The apparatus of claim 1, wherein the penetration depth is in a range of about 300 μm to about 600 μm.

4. The apparatus of claim 1, wherein the penetration depth is in a range of about 500 μm to about 2,000 μm.

5. The apparatus of claim 1, wherein the wavelength of the pulsed infrared laser beam is in a range of about 1.4 μm to 1.6 μm.

6. The apparatus of claim 1, wherein the wavelength of the pulsed infrared laser beam is in a range of about 1.8 μm to about 2.2 μm.

7. The apparatus of claim 1, wherein the wavelength of the pulsed infrared laser beam is about 1.875 μm.

8. The apparatus of claim 1, wherein the wavelength of the pulsed infrared laser beam is about 1.45 μm.

9. The apparatus of claim 1, wherein the wavelength of the pulsed infrared laser beam is about 1.94 μm.

10. The apparatus of claim 1, wherein the optical medium is adapted to be positioned at the predetermined distance to deliver the pulsed infrared laser to reach primarily layers I and II of neural tissues of the stimulation site where inhibitory neurons are a predominant cellular component.

11. The apparatus of claim 1, wherein the optical medium is adapted to be positioned at the predetermined distance to deliver the pulsed infrared laser to reach primarily layers III, IV, V, and VI of neural tissues of the stimulation site where excitatory neurons are a predominant cellular component.

12. The apparatus of claim 1, wherein the optical medium is adapted to be positioned at the predetermined distance to deliver the pulsed infrared laser to the stimulation site that has primarily inhibitory circuits and the evoked responses are primarily inhibitory neural responses.

13. The apparatus of claim 1, wherein the optical medium is adapted to be positioned at the predetermined distance to deliver the pulsed infrared laser to the stimulation site that has primarily excitatory circuits and the evoked responses are primarily excitatory neural responses.

14. The apparatus of claim 1, wherein the optical medium includes one or more free optics.

15. The apparatus of claim 1, wherein the optical medium is an optical fiber.

16. The apparatus of claim 15, wherein the distance of the optical fiber from a surface of the stimulation site is in a range of 0 to about 1,000 μm.

17. The apparatus of claim 15, wherein the optical fiber has a predetermined diameter and is configured to be positioned at the predetermined distance from the stimulation site such that the infrared laser delivered through the optical fiber covers a surface of the stimulation site entirely.

18. The apparatus of claim 17, wherein the diameter of the optical fiber is in a range of about 5 um to about 1,000 μm.

19. The apparatus of claim 17, wherein the numerical aperture of the optical fiber is in a range of about 0.1 to about 0.4.

20. The apparatus of claim 17, wherein the diameter of the optical fiber is about 400 μm and the numerical aperture of the optical fiber is about 0.22.

21. The apparatus of claim 17, wherein the optical fiber is configured to cover a surface of the stimulation site that has a spot size in a range of about 5 μm to about 2,000 μm.

22. The apparatus of claim 1, wherein the generator is configured to generate the pulsed infrared laser having a repetition rate in a range of about 1 Hz to about 500 Hz.

23. The apparatus of claim 1, wherein the generator is configured to generate the pulsed infrared laser having a repetition rate in a range of about 50 Hz to about 200 Hz.

24. The apparatus of claim 1, wherein the generator is configured to generate the pulsed infrared laser having a predetermined pulse width in a range of about 5 ps to about 5 ms.

25. The apparatus of claim 1, wherein the generator is configured to generate the pulsed infrared laser radiation having a constant pulse width of 250 μs.

26. The apparatus of claim 1, wherein the generator is configured to generate the pulsed infrared laser having a radiant exposure in a range of about 0.01 J/cm$^2$ to about 1.00 J/cm$^2$.

27. The apparatus of claim 1, wherein the optical medium is configured to deliver the pulsed infrared laser to the stimulation site that is positioned at a distance from a region of interest in a range of about 0 to about 2 mm.

28. The apparatus of claim 1, wherein the optical medium is configured to deliver the pulsed infrared laser to the stimulation site that is positioned at a distance from a region of interest in a range of about 0 to about 1 mm.

29. The apparatus of claim 1, wherein the imaging system comprises:
an imaging device acquiring image frames of the target; and
an imaging computer separate from the control computer, the imaging computer being configured to execute an imaging software code, wherein the imaging software code, when executed, is configured to:
specify the condition of the target based on the image frames of the target, wherein the condition of the target is specified as stimulus condition or blank condition, and
when the condition of the target is specified as the stimulus condition, send a signal to the control computer to initiate the control software code at the control computer.

30. The apparatus of claim 29, wherein the imaging device is a charge-coupled device (CCD) camera.

* * * * *